United States Patent
Fenn et al.

(10) Patent No.: US 6,807,446 B2
(45) Date of Patent: Oct. 19, 2004

(54) MONOPOLE PHASED ARRAY THERMOTHERAPY APPLICATOR FOR DEEP TUMOR THERAPY

(75) Inventors: Alan J. Fenn, Wayland, MA (US);
John Mon, Silver Spring, MD (US);
Dennis Smith, Ellicott City, MD (US)

(73) Assignee: Celsion Corporation, Columbia, MD (US)

(*) Notice: Subject to any disclaimer, the term of this patent is extended or adjusted under 35 U.S.C. 154(b) by 64 days.

(21) Appl. No.: 10/233,012

(22) Filed: Sep. 3, 2002

(65) Prior Publication Data

US 2004/0044385 A1 Mar. 4, 2004

(51) Int. Cl.[7] .................................................. A61N 5/02

(52) U.S. Cl. ........................ 607/101; 606/33; 607/156
(58) Field of Search ................................ 607/100–154, 607/96

(56) References Cited

U.S. PATENT DOCUMENTS

| | | | |
|---|---|---|---|
| 4,462,412 A | 7/1984 | Turner | |
| 4,589,423 A | 5/1986 | Turner | |
| 5,101,836 A | 4/1992 | Lee | |
| 5,251,645 A | 10/1993 | Fenn | |
| 5,441,532 A | 8/1995 | Fenn | |
| 5,540,737 A | 7/1996 | Fenn | |
| 5,810,888 A | 9/1998 | Fenn | |
| 6,200,598 B1 | 3/2001 | Needham | |
| 6,470,217 B1 * | 10/2002 | Fenn et al. | 607/101 |
| 2002/0193849 A1 * | 12/2002 | Fenn et al. | 607/89 |
| 2003/0004454 A1 * | 1/2003 | Fenn et al. | 604/20 |

FOREIGN PATENT DOCUMENTS

WO    WO 95/14505    6/1995

OTHER PUBLICATIONS

Gerhard et al., "Short Term hyperthermia: In Vitro Survival of Different Human Cell Lines after Short Exposure to Extreme Temperatures", Cancer Therapy by Hyperthermia and Radiation, Streffer C, editor, Baltimore–Munich: Urban & Schwarzenberg, pp. 201–203, 1978.

Harmon et al., "Cell Death Induced in a Murine Mastocytoma by 42–47° C. Heating in vitro: Evidence that the Form of Death Changes from Apoptosis to Necrosis Above a Critical Heat Load", Int. J. Radiat. Biol., vol. 58, No. 5, 845–857, 1990.

Turner et al., "Future Trends in Heating Technology of Deep–Seated Tumors", Recent Results in Cancer Research, vol. 107, pp. 249–262, 1988.

(List continued on next page.)

Primary Examiner—Linda C. M. Dvorak
Assistant Examiner—Henry M Johnson, III
(74) Attorney, Agent, or Firm—Venable LLP; Catherine M. Voorhees

(57) ABSTRACT

A monopole phased array thermotherapy applicator radiating radiofrequency energy for inducing a temperature rise in a target within a body includes a plurality of monopole elements each for transmitting electric-field radiation; a metallic waveguide with an RF reflecting ground plane surface with a plurality of circular holes for mounting the monopole elements where the metallic waveguide forms an aperture for receiving a body to be treated; a waveform generator providing a source of electric field coupled to each monopole radiating element through a respective phase and power weighting network; at least one electric field probe positioned on a skin surface of the body for detecting electric field radiation from the plurality of monopole elements; and a controller circuit coupled to the electric field probe received feedback signals to adjust the phase and power delivered to the plurality of monopole elements so that one or more adaptive nulls are formed on the surface of the body and a focus is formed at the target tissue to be treated with thermotherapy.

41 Claims, 22 Drawing Sheets

OTHER PUBLICATIONS

Shum et al., "Phototriggering of Liposomal Drug Delivery Systems", Advanced Drug Delivery Reviews 53, pp. 273–284, 2001.

Straube et al., "Phase Stability of a Clinical Phased Array System for Deep Regional Hyperthermia", Int. J. Hyperthermia, vol. 11, No. 1, pp. 87–93, 1995.

Fenn et al., "Noninvasive Monopole Phased Array for Hyperthermia Treatment of Cranial–Cavity and Skull–Base Tumors: Design, Analysis, and Phantom Test", Proceedings of the Annual International Conference of the IEEE Engineering in Medicine and Biology Society, vol. 15, Part 3, pp. 1453–1454, 1993.

Gross et al., "Applied Potential Tomography and Adaptive Control of Phased Microwave Systems", Proceedings of the 14th Annual Meeting of the North American Hyperthermia Society, Nashville, TN, 1994, p. 110.

Von Hippel et al., Dielectric Analysis of Bio–Materials, Massachusetts Institute of Technology, Laboratory for Insulation Research, Technical Report 13, pp. 1–20, AD–769–843.

Fenn et al., Improved Localization of Energy Deposition in Adaptive Phased–Array Hyperthermia Treatment of Cancer, The Journal of Oncology Management, vol. 7(2), pp. 22–29, 1998.

1994 International Symposium on Electromagnetic Compatibility, Sendai, Japan, pp. 566–569.

Sapareto et al., Thermal Dose Determination in Cancer Therapy, International Journal of Radiation Oncology Biology Physics, vol. 10, pp. 787–800, 1984.

Vitrogan, Elements of Electric and Magnetic Circuits, Rinehart Press, San Francisco, pp. 31–34, 1971.

* cited by examiner

MONOPOLE PHASED ARRAY THERMOTHERAPY APPLICATOR FOR DEEP TUMOR THERAPY

BACKGROUND OF THE INVENTION

The present invention generally relates to an apparatus for a monopole phased array thermotherapy applicator employed in deep heating of cancerous, precancerous, or benign tumors or infected or diseased tissue, such as arthritic tissue and tissue involving the human immunodeficiency virus (HIV) in a patient's body.

The most difficult aspect of administering thermotherapy to deep organs in the body is to provide sufficient heating of the deep organ without burning the skin. Methods for producing an adaptively focused electromagnetic energy beam at a deep tumor position have been described in U.S. Pat. Nos. 5,251,645, 5,441,532, 5,540,737, and 5,810,888, all of which are incorporated herein by reference.

U.S. Pat. No. 5,251,645 describes an adaptive RF hyperthermia phased array that uses feedback measurements from noninvasive electric field sensors to null or reduce undesirable temperature hot spots in healthy tissue, while focusing the array radiation on a tumor. U.S. Pat. No. 5,441,532 describes a monopole phased array applicator device used to heat deep seated tumors using RF or microwave focusing while simultaneously minimizing the occurrence of temperature hot spots by using adaptive nulling. U.S. Pat. No. 5,540,737 describes an adaptive monopole waveguide phased array on opposite sides of the compressed breast to heat deep seated tumors in the breast. U.S. Pat. No. 5,810,888 describes a monopole phased array for targeted drug delivery to tumors by adaptively heating and activating thermosensitive liposomes to release drugs into the tumor.

Deep tissue heating may result in burns to superficial tissues and as a result, it is particularly challenging to avoid burning superficial tissues while heating a deep tumor. Tumors that may require deep heating include those in the liver, lung, pancreas, ovaries, rectum, prostate, breast, and stomach. Further, regional heating is usually required as deep tumors are often advanced and therefore large in size. It is known in the art that radiofrequency (RF) hyperthermia for deep tumor treatments, in the range of about 43 to 46 degrees Celsius, is usually combined with either radiation therapy or chemotherapy for a synergistic effect. As developed in U.S. Pat. No. 5,810,888, thermotherapy can be also be used in adaptive phased array targeted drug delivery to selected tissues via thermosensitive liposomes, which are lipid bubbles containing a drug that is released at temperatures in the range of about 39 to 45 degrees Celsius. The assignee's method may be used with a recently developed temperature sensitive liposome formulation with chemotherapy agents such as doxorubicin as described in U.S. Pat. No. 6,200,598 "Temperature Sensitive Liposomal Formulation," Mar. 13, 2001 to Needham, in which drug agents are released at temperatures of approximately 39 to 45 degrees Celsius. Direct killing of cancerous tissue may be achieved with temperatures in the range of about 43 to 50 degrees Celsius. Specifically, cell kill may be induced by apoptosis in the range of about 43 to 45 degrees Celsius and by necrosis in the range of about 45 to 50 (or more) degrees Celsius (Gerhard et al., "Short Term Hyperthermia: In Vitro Survival of Different Human Cell Lines After Short Exposure to Extreme Temperatures", *Cancer Therapy by Hyperthermia and Radiation*, Streffer C, editor, Baltimore-Munich: Urban & Schwarzenberg. pages 201–203, 1978; and Harmon et al, "Cell Death Induced in a Murine Mastocytoma by 42–47° C. Heating in vitro: Evidence that the Form of Death Changes From Apoptosis to Necrosis Above a Critical Heat Load", *Int J Radiat Biol* vol. 58, pages 854–858, 1990). As direct killing of tissue cells may be achieved with temperatures in the range of 43 to 50 degrees Celsius, the challenge to avoid burning superficial tissues while heating the tumor still needs to be solved.

Thermotherapy at RF frequencies in the range of about 50 to 300 MHz with a large diameter ring array (about 1.5 to 3 times the diameter of the human body) is commonly suggested for deep tumor heating. A ring phased array composed of four waveguides with a coupling bolus for deep tumor heating was first introduced by von Hippel in 1973 (von Hippel et al., Dielectric Analysis of Bio-Materials, Massachusetts Institute of Technology, Laboratory for Insulation Research, Technical Report 13, pp. 16–19, AD-769 843). A dipole ring phased array concept for deep tumor heating has been described by Turner in U.S. Pat. No. 4,589,423, as well as in an article by Turner, P. F., Schaefermeyer, T., and Saxton, T. (Future Trends in Heating Technology of Deep-Seated Tumors, *Recent Results in Cancer Research*, vol. 107, pages 249–262, 1988).

One of the difficulties of treating patients with a large-diameter hyperthermia array without a waveguide enclosure is the requirement for a large water bolus to couple the RF energy in toward the body. The mass of the large water bolus resting on the patient's body may be uncomfortable to the patient. A metallic shielded room often must enclose the hyperthermia apparatus due to stray radiation. Without a metallic waveguide enclosure, the array has the potential for stray RF energy radiating along the longitudinal axis of the patient creating potential comfort and safety concerns. Thus, a metallic shielded room is likely to be required to prevent stray RF energy from interfering with other electronic equipment in systems without a waveguide enclosure.

SUMMARY OF THE INVENTION

The above shortcomings are solved by the monopole phased array thermotherapy applicator according to the invention. The monopole phased array applicator radiates radiofrequency energy to induce a temperature rise in targeted tissue within a body and includes a plurality of monopole elements that each transmit electric-field radiation, a metallic waveguide with an RF reflecting ground plane surface with a plurality of circular holes for mounting the monopole elements, a waveform generator providing a source of electric field coupled to each monopole element through a respective phase and power weighting network, at least one electric field probe positioned on the skin surface of the patient's body for detecting electric field radiation from the plurality of monopole elements, and a controller circuit coupled to the electric field probe that receives feedback signals to adjust the phase and power delivered to the plurality of monopole elements so that one or more adaptive nulls are formed on the surface of the body and a focus is formed at the target tissue to be treated.

An adaptive thermodynamic RF monopole phased array antenna applicator surrounds a target body and provides minimally invasive heating of tissue in the range of approximately 39 to 50 degrees Celsius. This applicator can be used for heat-alone treatment, to activate thermosensitive liposomes and preferentially deliver drugs to regions deep in the body, or it can be used synergistically with radiation therapy, chemotherapy, drugs, or gene therapy. The use of a monopole phased array permits focused heating of large tissue masses deep within the human body and, at the same time, provides patient comfort. When the array is operating in the adaptive phased array mode, the power and phase delivered to the phased array antenna elements are computer controlled using feedback signals measured by noninvasive electric-field and temperature sensors placed outside the body (e.g., on the patient's skin and within the tissue region to be treated) to control a phase shifter and power amplifier network to adjust the phase and power delivered to the monopole elements to form one or more nulls on the patient's skin surface, while focusing energy at a deep tissue site to heat the deep tissue site to the range of 39 to 46 degree Celsius. The magnitude of the nulls formed on the patient's skin surface and the focus in the tissue treatment region may be controlled by an adaptive phased array fast acceleration gradient search computer algorithm that adjusts the phase and power delivered to the monopole elements. A fast acceleration adaptive nulling and focusing gradient search algorithm and monopole array applicator for deep tumor heating are disclosed in U.S. Pat. No. 5,810,888 to Fenn and can be used as a starting point.

Theoretically, the adaptive monopole phased array thermotherapy system is capable of clinically treating many different types of deep-seated tumors (cancerous and benign) such as those occurring in the prostate, breast, liver, rectum, colon, cervix, pancreas, stomach, bladder, lung, and other deep organ sites in the human body. This thermotherapy system can be used to target the delivery of drugs by heating the tissue and releasing drugs from thermosensitive liposomes circulating within the bloodstream in the vicinity of the targeted tissue. The same thermotherapy system can also be used in conjunction with target radiation thermotherapy to enhance the effectiveness of chemotherapy, drugs, and gene therapy.

In contrast with photodynamic therapy (Shum et al., Phototriggering of Liposomal Drug Delivery Systems, *Advanced Drug Delivery Review*, 2001, vol 53, pages 273–284.), which uses laser light to energize drugs or liposomal encapsulated drugs, deep heating with a noninvasive adaptive phased array thermotherapy system may be used to activate thermosensitive liposomes to concentrate a drug into a tumor and energize the drug. The word "thermodynamics" refers to the physics of the relationship between heat and other forms of energy. The therapy described here can thus be referred to as an adaptive phased array (APA) thermodynamic therapy (TDT).

DETAILED DESCRIPTION OF THE PREFERRED EMBODIMENTS

Figure 1:
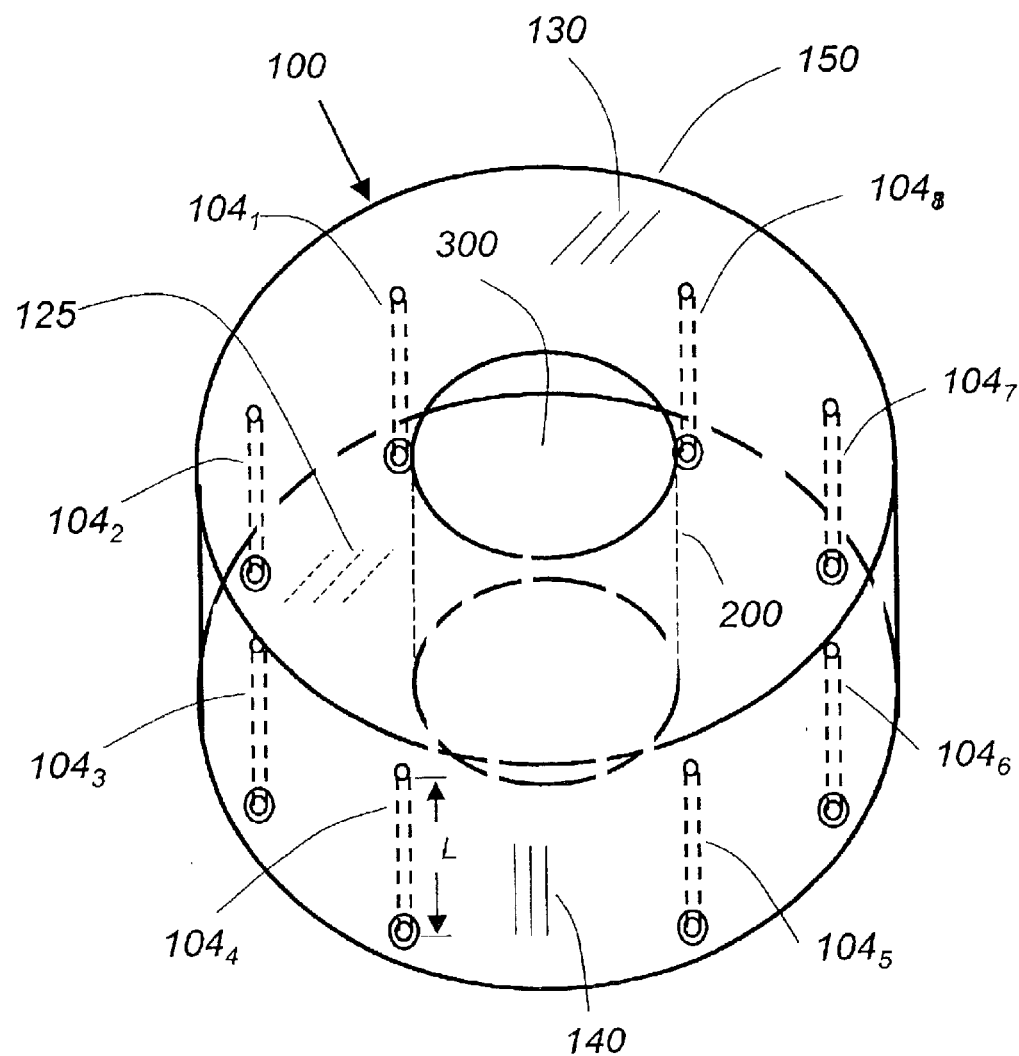
FIG. 1 is schematic view of a water-filled monopole ring array applicator.

The present invention is directed to a monopole phased array thermotherapy applicator and system that overcomes the shortcomings associated with known deep heating systems. A pictorial view of a water-filled monopole ring array applicator 100 for thermotherapy, according to one embodiment of the invention is depicted in FIG. 1. In the preferred applicator 100, there are eight monopole antenna elements 104 mounted in the interior portion of the metallic waveguide cavity 150. In the preferred embodiment, the radiating frequency is in the range of about 90 to 110 MHZ. Metallic waveguide cavity 150 is constructed so that the mounted monopole elements form a ring about a treatment aperture 300. In a preferred embodiment, the ring would be circular and have a diameter up to 90 cm. A more preferred diameter would be between about 50 to 70 cm. The metallic waveguide cavity is formed by a lower metallic flat plate 125 and an upper metallic flat plate 130, both with a central elliptical shaped aperture. A substantially rigid acrylic plastic tube 200 of an elliptical cross section is used to hold water within the metallic waveguide cavity section. The patient treatment aperture 300 is located at the central region of the monopole ring array.

Figure 2:
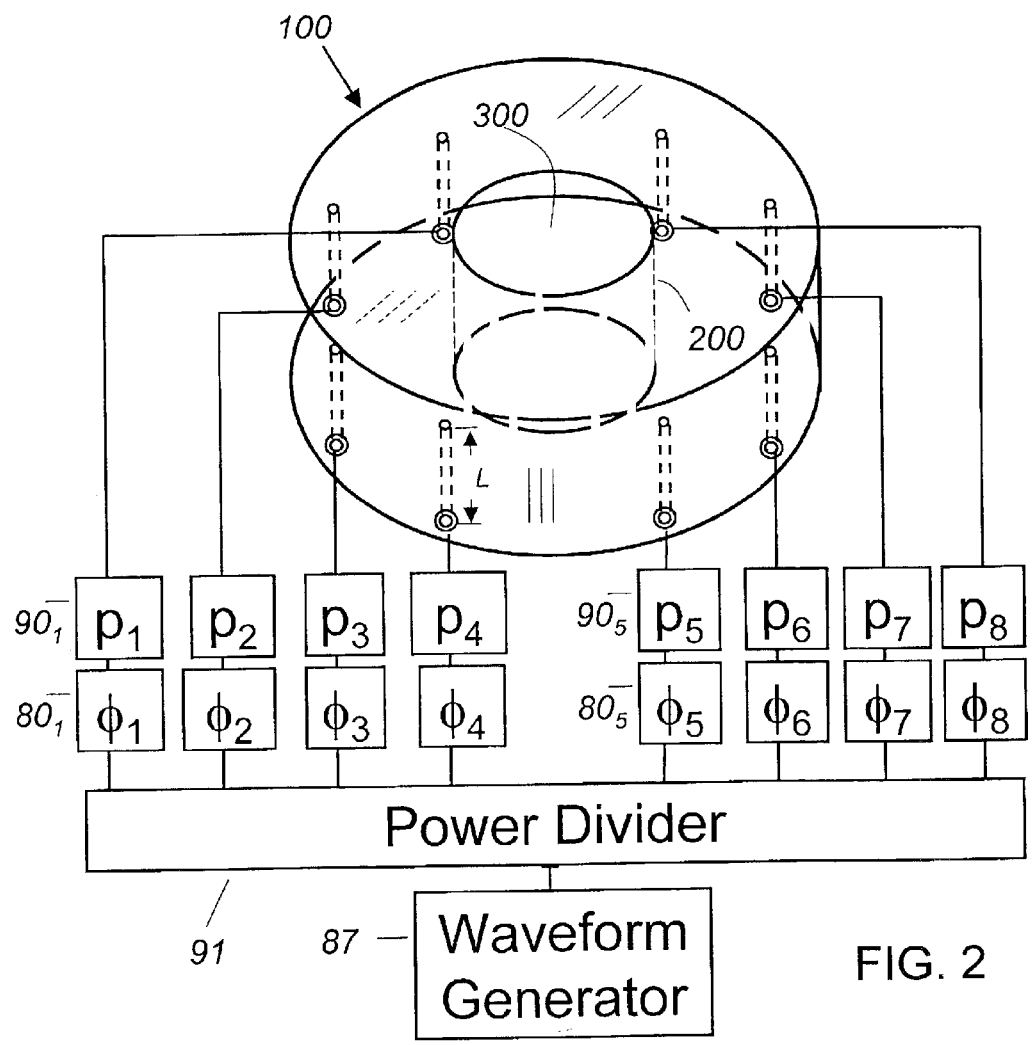
FIG. 2 shows a thermotherapy system according to one embodiment of the invention where the monopole array elements are each driven adaptively by RF phase shifter and power amplifier devices.

The monopole antenna elements 104 are parallel to each other and are located at a fixed distance from the cylindrical backwall 140 of the metallic waveguide cavity. For example, the monopole elements would be arranged in a ring and be spaced from about 6 to 10 cm from the reflecting ground plane behind each monopole element. In FIG. 2, the monopole array elements are each driven adaptively by RF phase shifter 80 ($\phi_1$, $\phi_2$, , $\phi_8$) and power amplifier 90 ($p_1$, $p_2$, ..., $p_1$) devices. RF signals such as continuous waves CW (oscillator), pulsed, or other waveforms suitable for thermotherapy are generated by a waveform generator 87 which divides into eight channels using a passive power divider 91.

Figure 3:
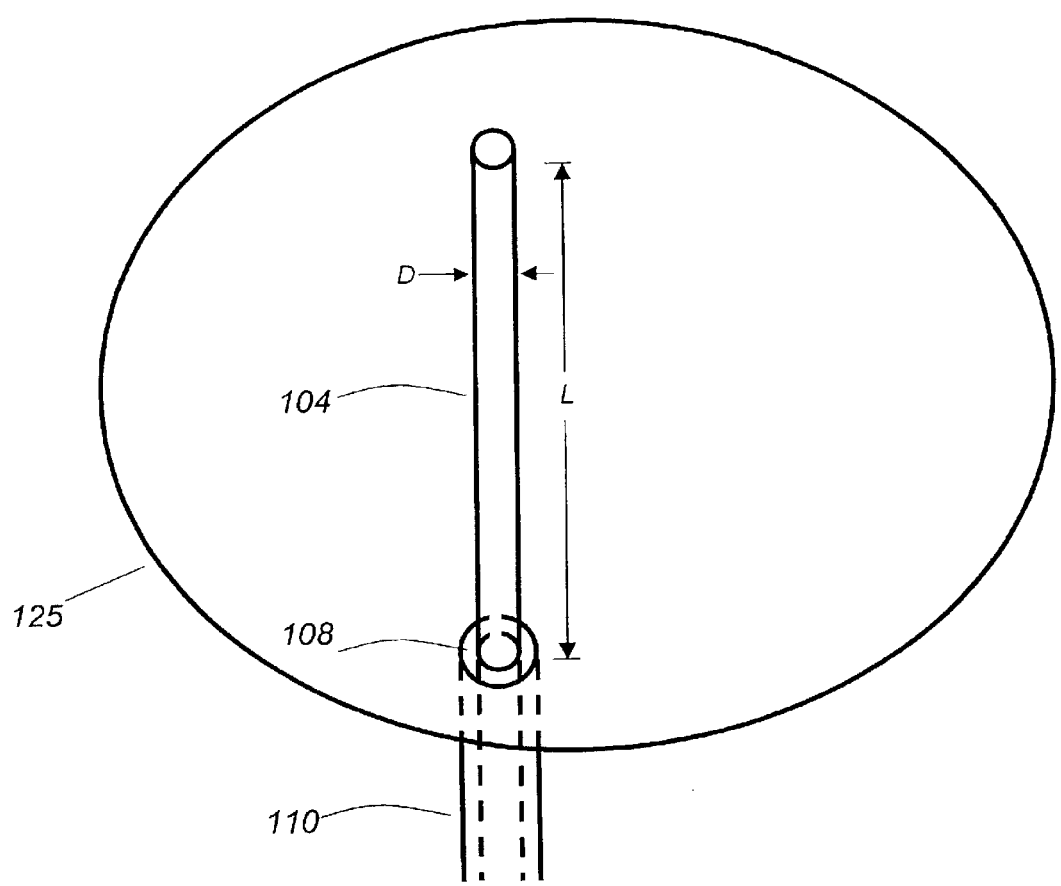
FIG. 3 shows a single monopole according to one embodiment of the invention.

A single monopole antenna element 104 with length L and diameter D is depicted in FIG. 3. The length L of a monopole antenna element 104 may be between approximately 7 to 12 cm long. The diameter D of a monopole antenna element 104 may be between approximately 0.1 to 0.5 cm. The monopole antenna element 104 is attached to the center conductor of a RF coaxial cable 110 forming a feed aperture 108 that illuminates the metallic conductor of monopole antenna element 104. The monopole conductor is oriented perpendicular to a metallic ground plane 125. The monopole antenna element 104 can be connected to the RF coaxial cable by means of a standard RF coaxial connector such as a type-N coaxial connector. The monopole feed aperture 108 equivalently is a circular hole in the metallic ground plane 125 for which the type-N coaxial connector mates with the ground plane 125.

In a preferred embodiment, the monopole element 104 is made of a cylindrical straight metallic wire or tube. In alternate embodiments, the monopole element 104 can be conically shaped or helically shaped. In another embodiment, a dipole parallel to the backwall 140 of the monopole array applicator 100 can also be used as an array element.

A monopole array design is desirable for a number of reasons including: patient comfort during set up and treatment, deep heating, real-time control of the focused heating pattern, and confinement of the longitudinal heating distribution. Also, stray radiation for the monopole phased array design according to the invention is minimal thereby reducing the need of an RF shielded room for treatments, as well as shielding the patient.

Patient Comfort

Figure 4:
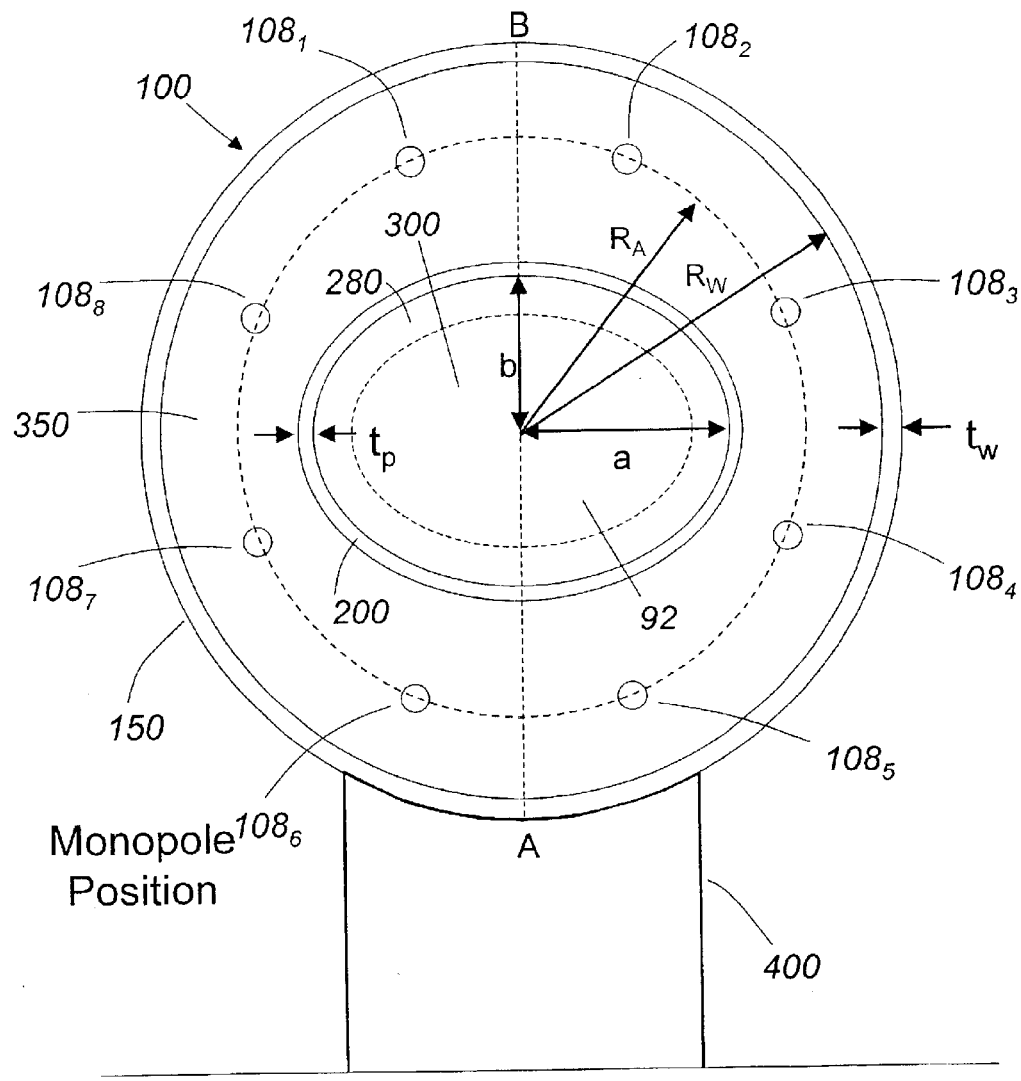
FIG. 4 schematically illustrates a monopole phased array applicator according to one embodiment of the invention.

A schematic diagram of the monopole phased array applicator 100 is shown in FIG. 4. The elliptical shaped acrylic plastic tube 200 has a thickness denoted $t_p$. A target body 92 is positioned within the aperture 300 of the monopole array applicator 100. In the embodiment shown in FIG. 4, an air-cooled air gap region 280 is used to couple RF energy into the deep tissues of the patient. The air gap 280 may be cooled by means of air conditioned or room temperature air emitted through a plurality of tubes or fans directed at the air gap. In an alternate embodiment shown in FIG. 5, a flexible water bolus is used to couple RF energy into the deep tissues of the patient. The monopole antenna element positions 108 are located on a circle (ring) with a radius denoted $R_A$. The inner radius of the metallic waveguide housing 150 is denoted $R_W$. The thickness of the metallic waveguide housing is denoted as $t_w$. The outer surface of the metallic waveguide housing 150 is supported by aluminum or another rigid support member 400. Rigid support member 400 may be moveable so that the monopole phased array applicator 100 may be moved prior to and/or after patient treatment. For example, rigid support member 400 may have wheels so that it can be moved horizontally from one location to another, or, the wheels may be used in conjunction with a track or rails that can guide the movement of the monopole array applicator 100 to traverse the patient positioning surface and improve positioning of the monopole antenna elements for accurate heating of a tumor. Magnetic locks, for example, can be employed to maintain the physician selected treatment position of the monopole array applicator. The patient treatment cross-sectional aperture is elliptically shaped with a major axis a and a minor axis b. In addition to the horizontal movement of the applicator, the applicator ring or portion of a ring is mounted on the track with an electrically operated vertical motion platform. This allows fine adjustment of the physical anatomical structure so that it is centered in the eye of the treatment aperture.

Figure 5:
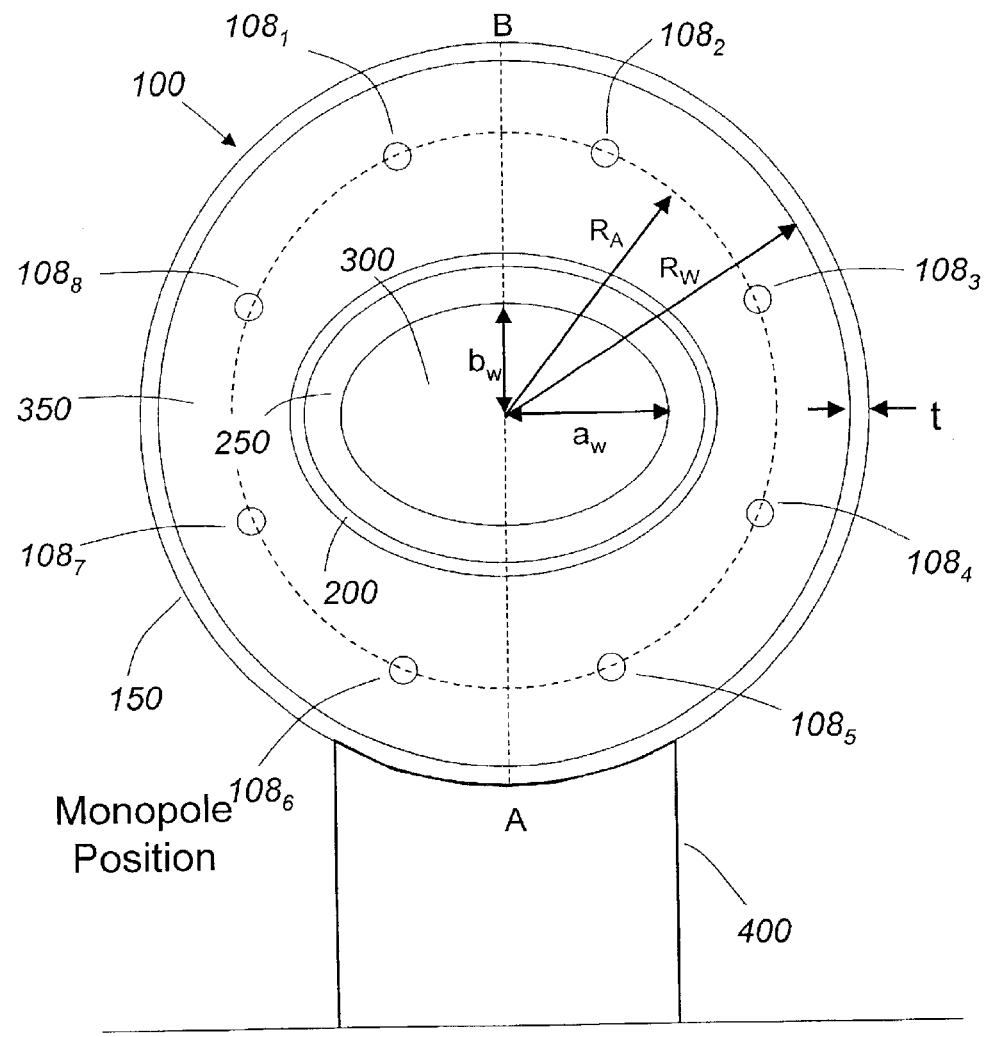
FIG. 5 is schematic illustration of an approximately elliptical-shaped water bolus.

In FIG. 5, an approximate elliptically shaped water bolus 250 consisting of a flexible plastic bag filled with circulating cooled distilled or deionized water is placed between the patient's torso and the acrylic aperture region 200 prior to thermotherapy. This treatment configuration has a smaller patient treatment aperture 300 when the dimensions of the major axis $a_w$ and the minor axis $b_w$ are compared to the air-cooled configuration in FIG. 4. According to the invention, the patient treatment aperture preferably should have a major axis between about 42 and 52 cm and a minor axis between about 30 and 38 cm.

The liquid-filled bolus may have a circumferential variable pressure to assist in cooling the surface of the body and modify blood flow, as well as couple RF radiation to the target body. That is, the pressure of the bolus may vary over its circumference depending on the treatment. It is envisioned that increased pressure via the bolus would decrease blood flow to the target body thereby slowing down the removal of heated blood from the target body treatment region to enhance delivery of the RF radiation heat/energy and to shape the region that is being heated.

Figure 6:
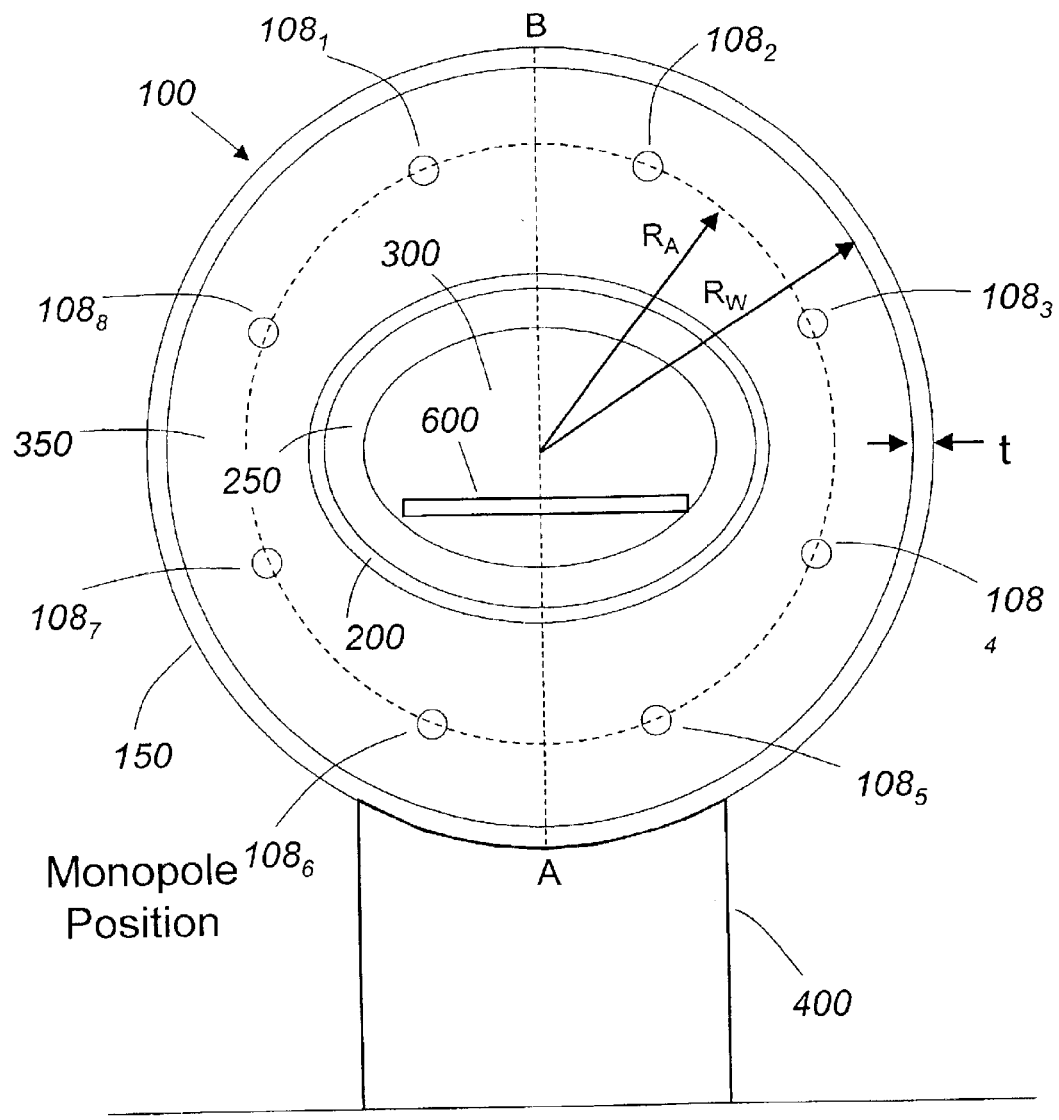
FIG. 6 is a schematic diagram of the monopole phased applicator with a patient support.
Figure 7:
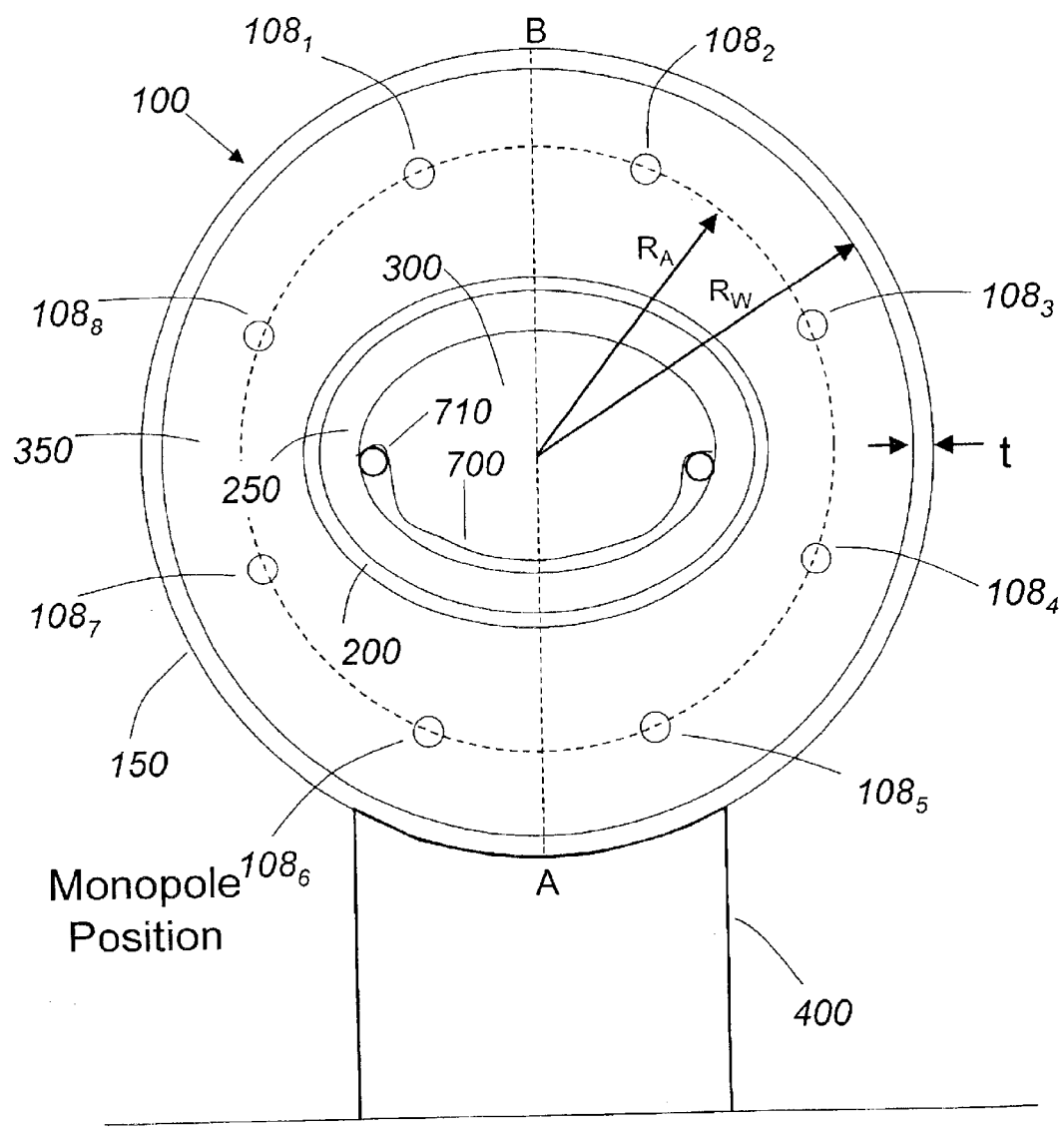
FIG. 7 is a schematic diagram of the monopole phased applicator with a cloth material suspended between two supports for supporting a patient.
Figure 8:
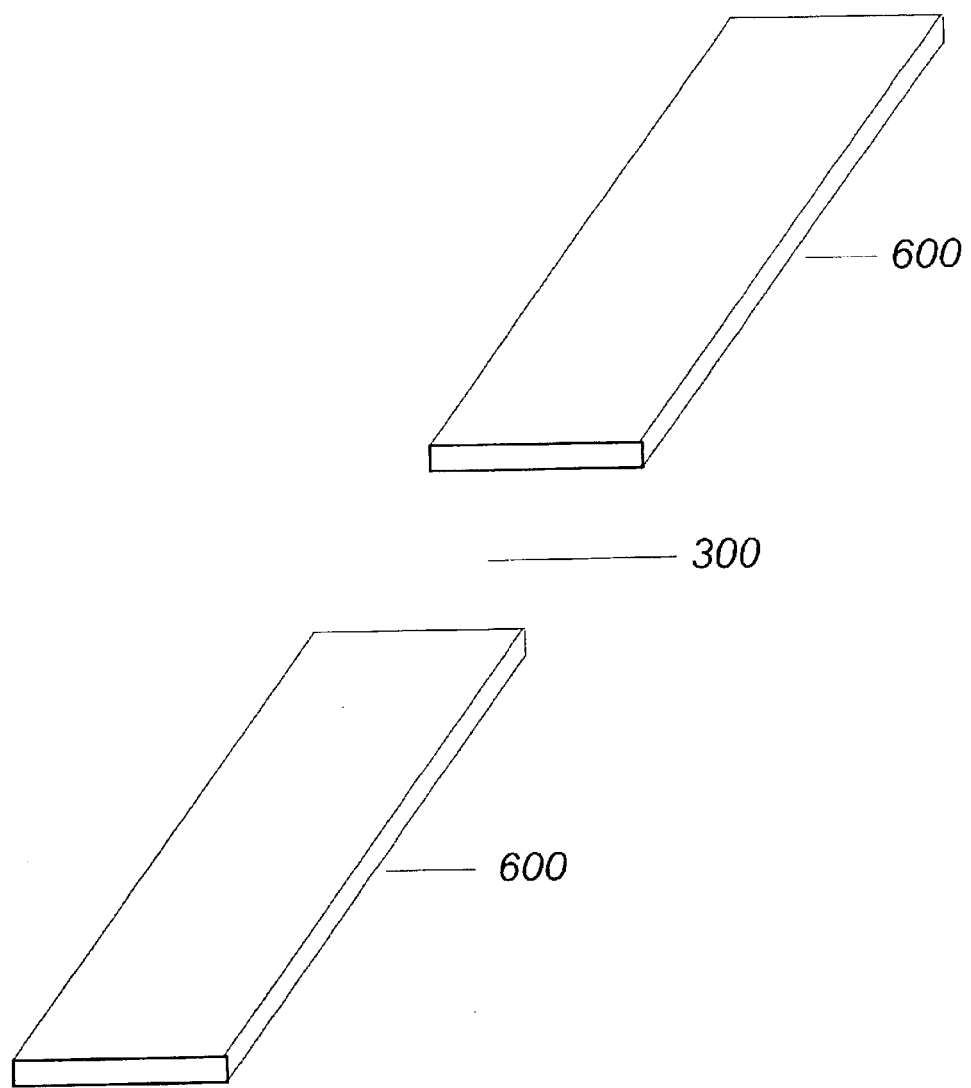
FIG. 8 illustrates a rigid support split into two sections to provide a treatment aperture according to another embodiment of the invention.
Figure 9:
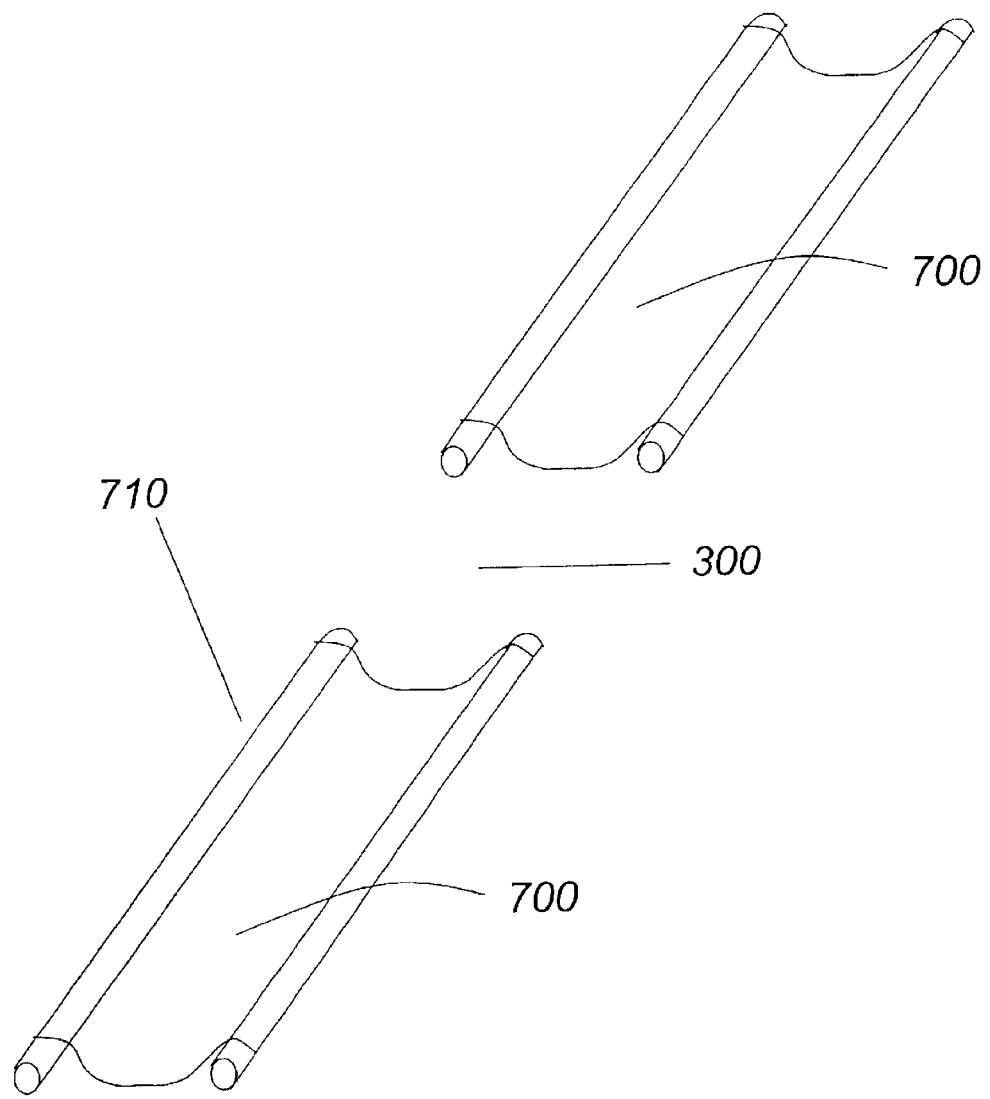
FIG. 9 shows a cloth support split into two sections to provide a treatment aperture according to yet another embodiment of the invention.
Figure 10:
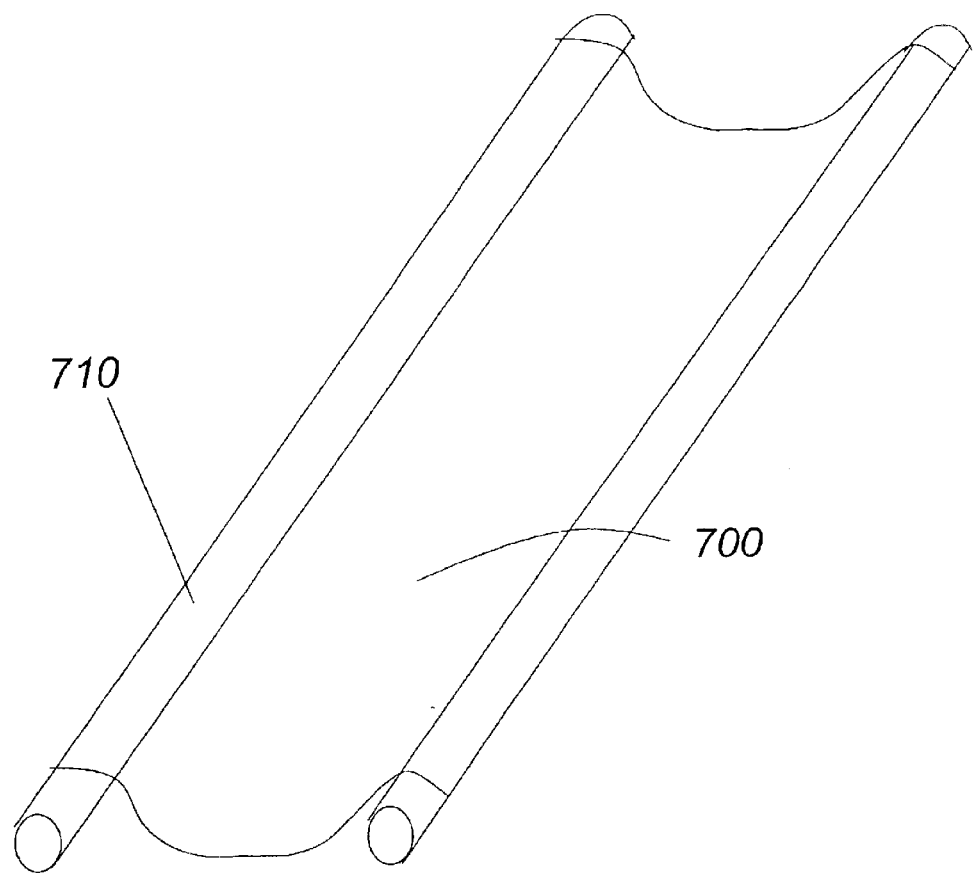
FIG. 10 shows a cloth support with no gap in another embodiment of the invention.

FIG. 6 shows a schematic diagram of the monopole phased array applicator 100 including a flat rigid patient support 600 that would be covered with a soft pad during patient treatments. The patient would typically lie supine or prone. In an alternate embodiment, FIG. 7 shows a schematic diagram of the monopole phased array applicator 100 including a Kevlar® (poly(p-phenyleneterephtalamide)) or cloth material 700 suspended between two cylindrical supports 710 for supporting the patient during treatment. The patient support 600 or 700 can be split into two sections to provide a treatment aperture 300 or gap that would be aligned mechanically with the treatment aperture as suggested in FIG. 8 and FIG. 9. The patient support, either 600 or 700, can be a single length covering the full length of the patient with no gap as suggested by FIG. 10. In a preferred embodiment, the materials used in supporting the patient are non-conducting. For example, the flat rigid patient support 600 or 700 may be fabricated from wood, plastic, or fiberglass. In addition, grounded metal material may be used in the patient supports 600 or 700 provided that the metal or other electrical conductor does not directly lie within the treatment aperture 300 of the monopole phased array applicator.

In addition to, or instead of, movement of the monopole array applicator, the patient support 600 or 700 may be movable within the aperture 300 of the monopole array applicator 100. Thus, the targeted tumor may be moved into an efficient alignment with the array of monopole antenna elements thereby resulting in a better thermotherapy treatment. The patient support 600 or 700, as well as the movable applicator, may be designed to move along the x, y and z axes. Thus, the monopole phased array applicator 100 would have the ability to scan the body and increase the ability to heat along all 3 axes.

Figure 11:
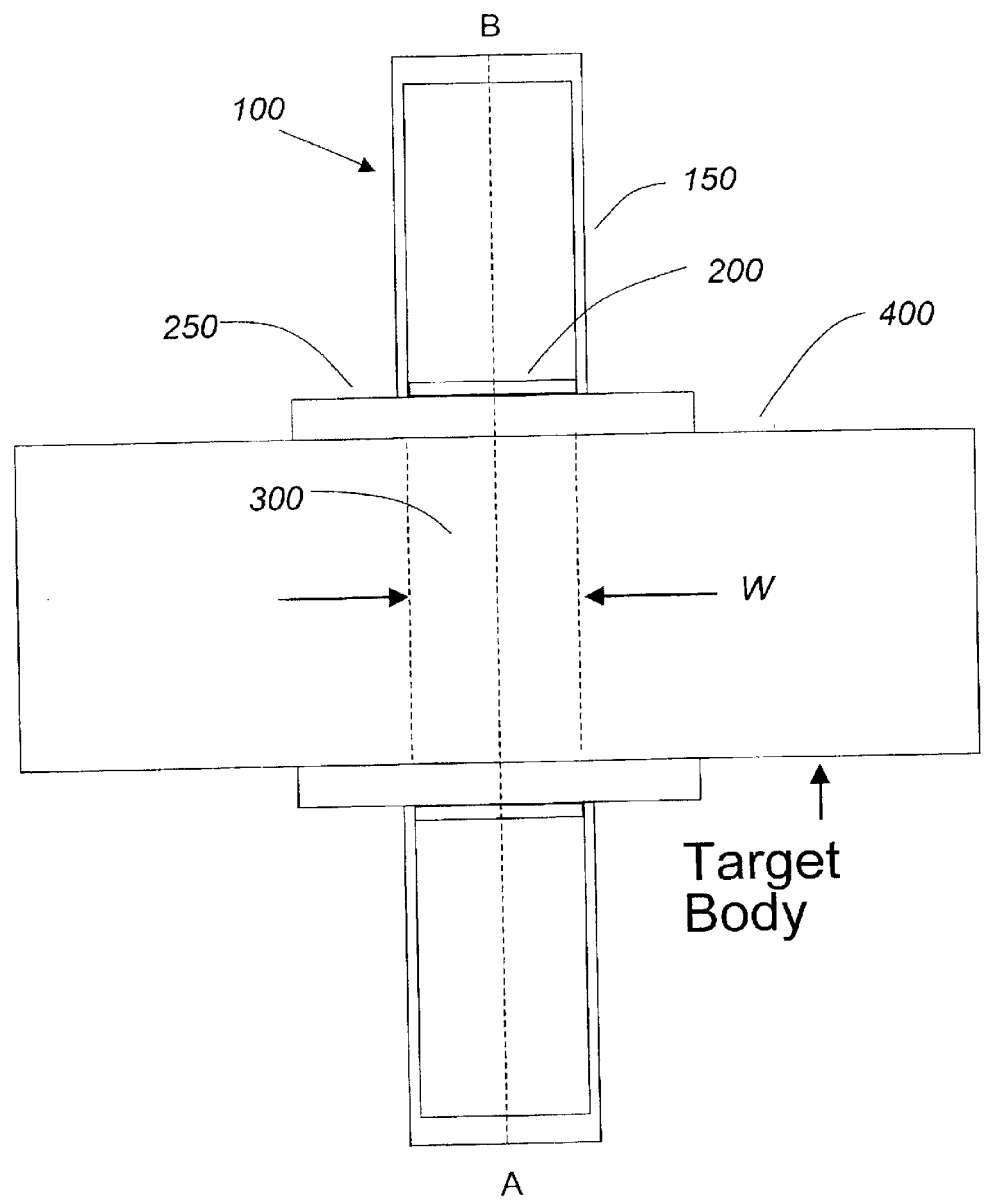
FIG. 11 is a side view of the monopole phased array applicator.
Figure 12:
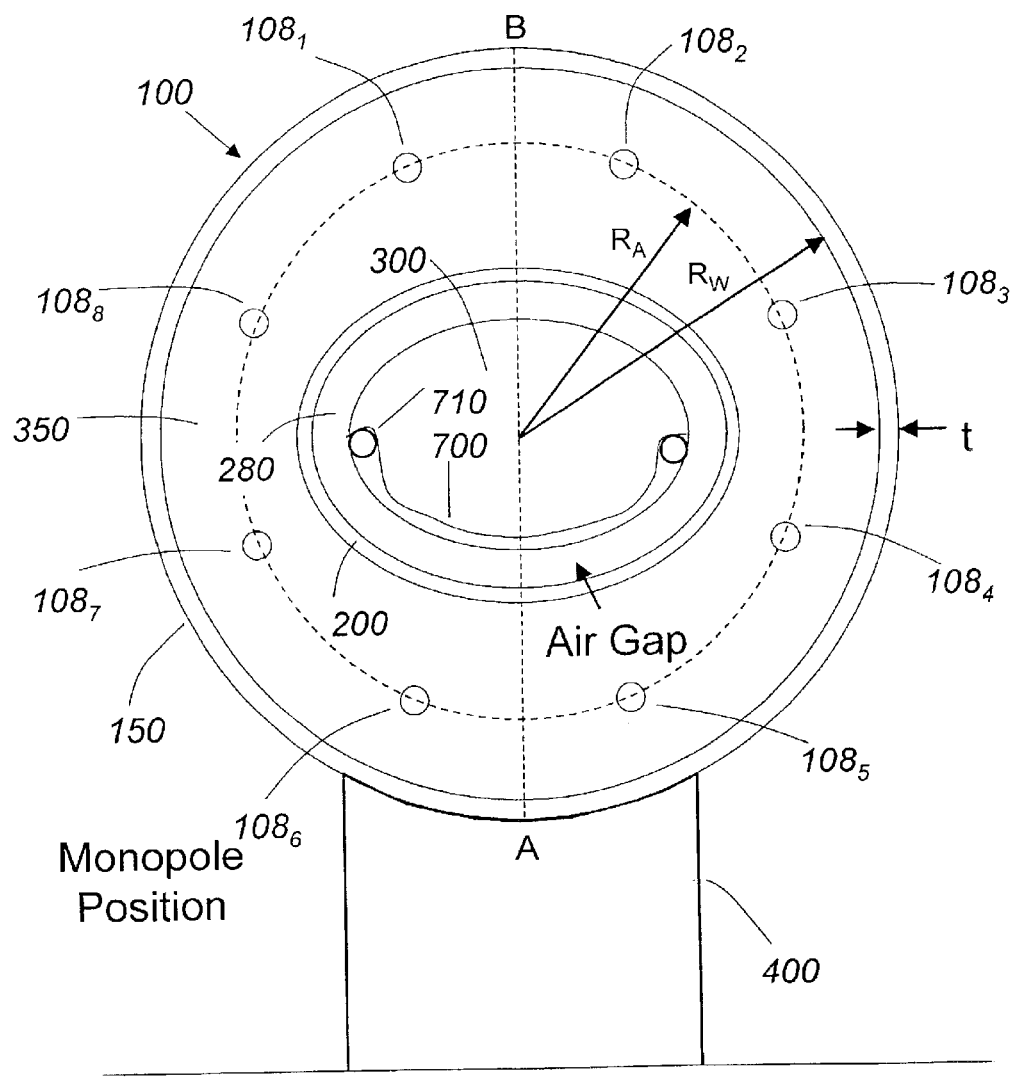
FIG. 12 illustrates an air gap surrounding the patient support in another embodiment.

FIG. 11 shows a side view of the monopole phased array applicator 100. The treatment aperture 300 is confined by the metallic waveguide structure to lie within approximately the longitudinal aperture dimension of the waveguide, denoted W. All of the mass associated with the metallic waveguide 150 and water 350 inside the waveguide is isolated from the patient. A moderately thick (ranging from approximately 4 to 10 cm depending on the patient cross section) flexible water bolus 250 may be used to couple the RF energy from the aperture of the waveguide to the torso. Since the applicator 100 is substantially rigid, only the mass of the water bolus 250 applies pressure to the target body (patient). The water bolus may use circulating cooled distilled or deionized water. In a preferred embodiment, a water bolus is used; however, in another embodiment shown in FIG. 12 no water bolus is used and an air gap 280 together with air cooling, via fans or tubes conducting refrigerated or room-temperature air, is used to maintain safe skin surface temperatures during thermotherapy. Another embodiment according to the invention would combine the water bolus and air gap techniques to couple the RF energy from the aperture of the waveguide to the target body. It is envisioned that an even smaller water bolus could be used if combined with the air gap technique.

The monopole phased array according to the invention is significantly different and may be more comfortable than an array of dipoles with a large water bolus fully filled and in contact with the patient as the mass of the bolus is often uncomfortable for the patient. Effectively larger diameter arrays adapted for deeper penetration are possible with a monopole array according to the invention since the size and mass are not an issue.

In another embodiment according to the invention, the waveguide cavity 150 that houses the monopole elements 104 made be fabricated from aluminum, or metallized fiberglass or plastic. The waveguide cavity may be made of a single piece or multiple pieces of conducting material that retains the desired electrical, radiating pattern and fluid containment principles of the fundamental design. Metallization of the fiberglass or plastic material may be continuous or may alternate with aluminum or other conducting mesh or conducting wires. To minimize the chance of any water leakage, it is desirable to fabricate the conducting cavity as a single piece or in multiple pieces that are tightly sealed together. For example, if three pieces of material are used, two aluminum or other conducting material plates would be parallel to one another and form the top 130 and bottom walls 125 of the applicator. The third aluminum or other conducting plate is rolled into a circular arc to form the curved backwall behind the monopole elements. A water-tight seal is critical for clinical operation. Thus, the aluminum plates should be mated using slots and flexible gaskets and then welded together. An acrylic (e.g., Plexiglas® (lightweight, transparent thermoplastic synthetic resin)), or fiberglass, aperture cover bent into the shape of the curved aperture seals and supports the water within the conducting cavity. It is necessary to have a solid aperture cover to keep the weight of the water from pressing against the patient.

Deep Heating Characteristics of a Large Ring Array of Monopole Elements

Figure 13:
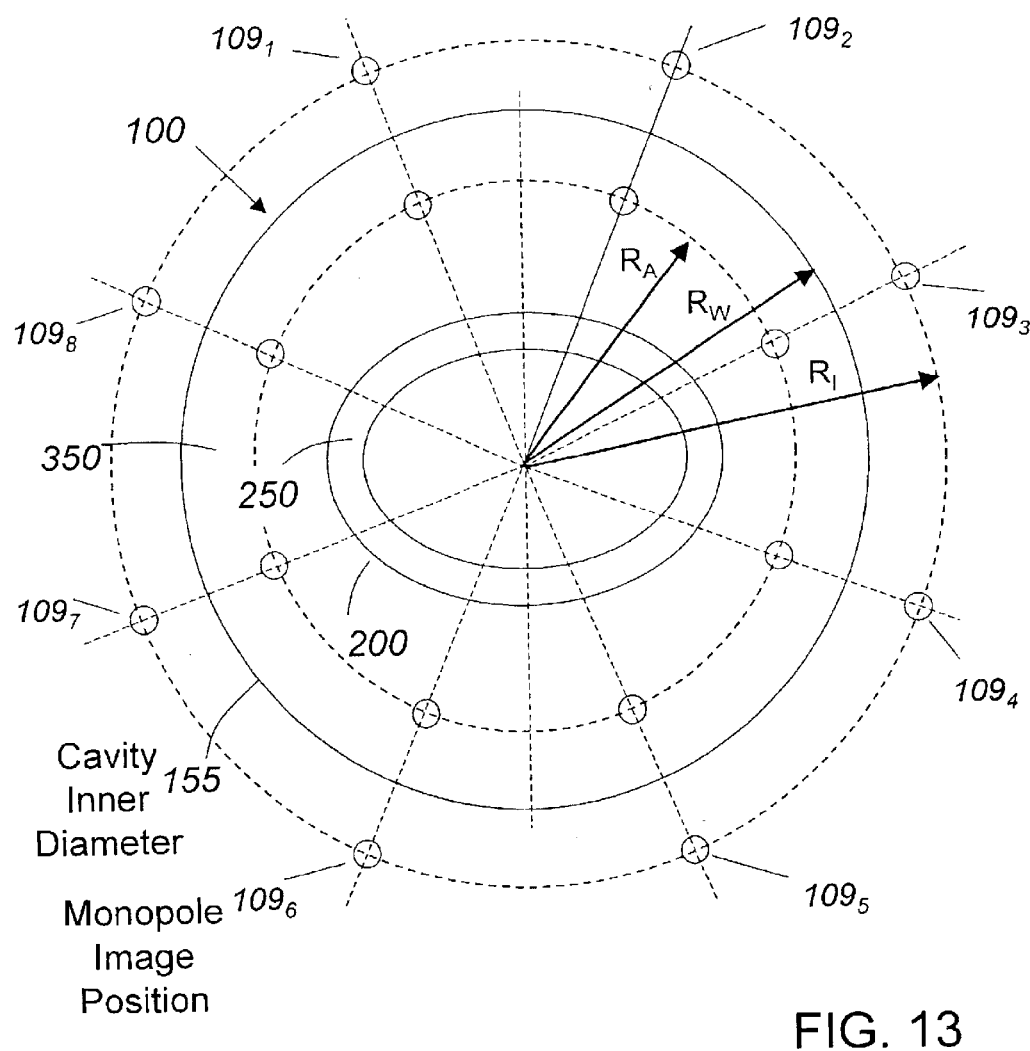
FIG. 13 depicts the cavity inner diameter of the monopole phased array applicator.

The specific absorption rate (SAR) is a parameter used in quantifying the heating performance of thermotherapy applicators. The SAR is proportional to the square of the magnitude of the electric field radiated by the thermotherapy applicator. With proper choice of the ring array diameter, it is possible to reduce the level of surface SAR compared to the SAR produced at depth in the tumor or treatment region. Fundamentally, this effect is due to spherical-wave versus plane-wave radiation. A plane wave attenuates rapidly in muscle tissue due to the dielectric loss of the tissue. For spherical waves, in addition to dielectric losses the wave attenuates inversely proportional to the radial distance R. Plane waves penetrate deeper than spherical waves since the (1/R) radial dependence of E-field attenuation with depth is removed. A plane wave is attenuated only by the loss due to dielectric material attenuation. A spherical wavefront can be made more planar by allowing the diameter of the ring array to grow. Thus, an effective 90 to 120-cm diameter ring array may yield deeper penetration compared to a 60 cm diameter ring array. The monopole phased array waveguide design makes this larger ring array possible. In FIG. 13, the reflecting surface 155 behind the active radiating monopole elements provides a secondary image array of monopoles 109 with a resulting effective larger array diameter. The effective radius, denoted $R_I$, of the image monopole array is equal to $$R_I = 2R_W - R_A. \qquad (1)$$

Referring to FIG. 13, in the preferred embodiment the radius of the monopole array approximately is $R_A$=30 cm and the reflecting wall surface has an approximate radius $R_W$=38 cm, thus from Equation (1) the image array radius would be approximately $R_I$=46 cm. In the preferred embodiment, the distance from the monopole to the reflecting backwall 155 would be about 8 cm.

Real-Time Control in Thermodynamic Therapy

Pre-treatment planning is sometimes discussed in the literature in terms of controlling actual hyperthermia sessions where patients are heated. This approach generally is not acceptable since theoretical treatments and actual treatments can differ significantly. During hyperthermia treatments, phase drift in the phase shifters and power amplifiers as well as in the cables, and connectors and human body itself can lead to significant phase focusing errors (Straube et al., Phase Stability of a Clinical Phased Array for Deep Regional Hyperthermia, *International Journal of Hyperthermia*, Vol. 11(1), pages 87–93, 1995). As shown schematically in FIG. 14, the instant invention uses a reliable approach by employing real-time feedback signals 114 from E-field and temperature sensors 112 to control the E-field and temperature distribution in a patient. An adaptive monopole phased array 100 with real-time feedback 114 and control 116 is a potentially viable approach for clinical treatments.

Figure 14:
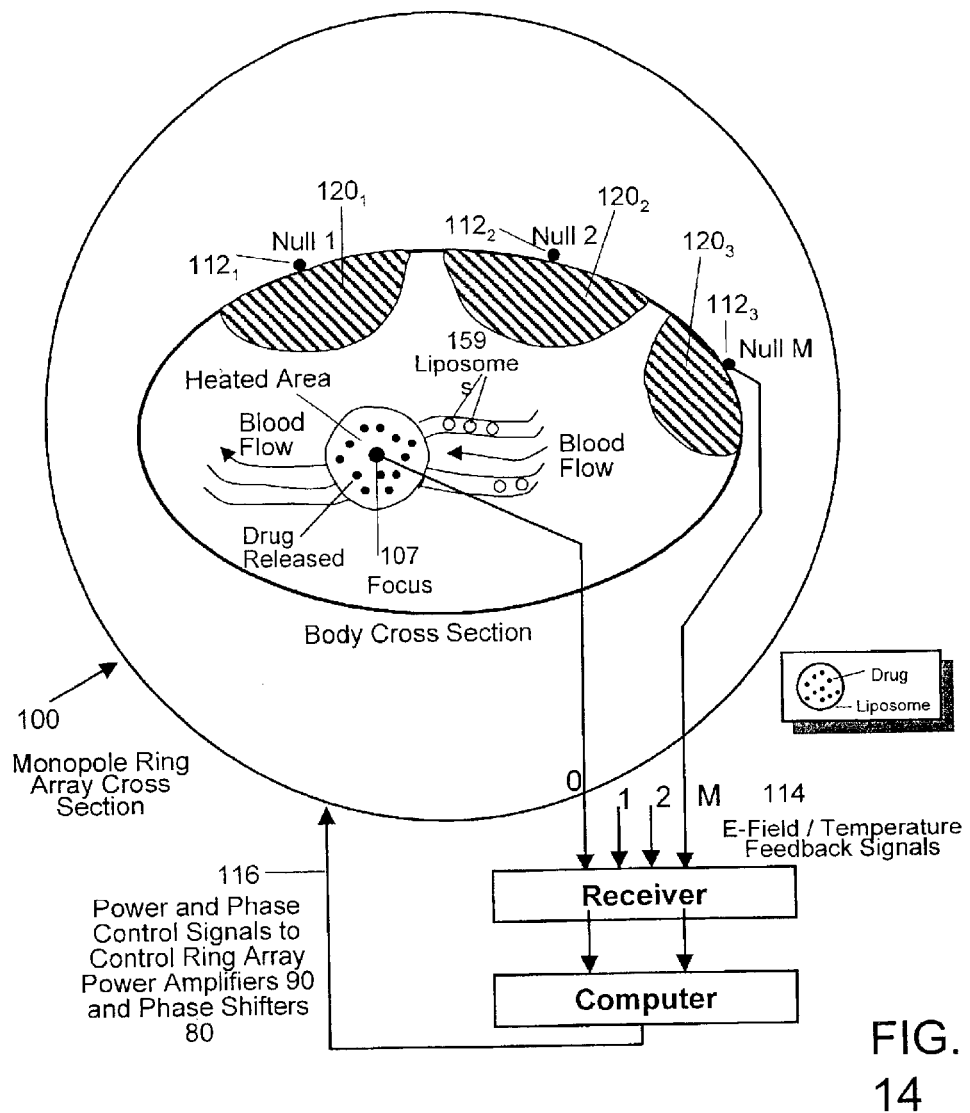
FIG. 14 schematically shows using real-time feedback signals from E-field and temperature sensors to control the same during treatment.

In the preferred embodiment illustrated in FIG. 14, thermosensitive liposomes 159 containing a drug agent are infused into the bloodstream of a patient and travel toward the tissue to be treated. The RF radiation from the adaptive monopole phased array applicator 100 elevates the temperature of the target tissue at the focus 107 thereby heating thermosensitive liposomes and releasing the drug agent within the liposome. Adaptive focusing for heating a deep tumor basically is an adjustment of the phase shift of each monopole element of the phased array so that the E-field is maximized forming a focus 107 at the tumor. However, it is expected that adaptive focusing alone may not be adequate in general to avoid superficial hot spots.

Noninvasive adaptive nulling of the superficial fields can be accomplished using feedback from E-field sensors mounted on the skin surface at one or more null positions at the probes 112 and by controlling the power and phase to each radiating monopole antenna. The null zones 120 surrounding each surface E-field sensor penetrates into the body and protect the skin and subcutaneous tissues. Demonstrations of adaptive nulling and deep heating in phantoms have been conducted successfully, for example on a 4-channel ring array of dipoles (Fenn et al, Improved Localization of Energy Deposition in Adaptive Phased-Array Hyperthermia Treatment of Cancer, *The Journal of Oncology Management*, Vol. 7(2), pages 22–29, 1998).

Control of the RF power delivered to the monopole elements in the array is determined in real-time by either temperature feedback measurements to set the desired temperature and thermal dose in the tumor, or by controlling the total delivered microwave energy dose based on results of clinical studies while maintaining tolerable and safe skin surface temperatures. Temperature measurements in the tumor may be accomplished by means of an invasive temperature sensor inserted in the tumor or by non-invasive thermometry means.

Confinement of the RF Radiation

In a preferred embodiment, the deep-heating monopole phased array is composed of a ring array of eight RF radiating monopole antenna elements. The ring array elements are resonant monopoles approximately one-quarter wavelength long fed by the center pin of a standard coaxial connector (Fenn et al., Noninvasive Monopole Phased Array for Hyperthermia Treatment of Cranial-cavity and Skull-base Tumors: Design, Analysis, and Phantom Tests, *Proceedings of the International Conference of the IEEE Engineering in Medicine and Biology Society*, San Diego, Calif., Oct. 28–31, 1993, Vol. 15, Part 3, pages 1453–1454; Fenn et al., Minimally Invasive Monopole Phased Arrays for Hyperthermia Treatment of Breast Carcinomas: Design and Phantom Tests, 1994 *International Symposium on Electromagnetic Compatibility*, Sendai, Japan, pages 566–569). The monopole elements radiate within a parallel-plate waveguide structure filled with distilled or deionized water. A metallic backwall, cylindrical in shape, is used to reflect RF energy towards the patient's torso. The radiofrequency energy is in the range of about 80 to 150 MHz. For deep penetration into tissues, the desired radiating frequency is in the range of about 100 to 150 MHz (note: the frequency range 88 to 108 MHz is the FM radio band). A simple test to determine whether the monopole phased array antenna will interfere with FM radio reception is to place a standard FM radio outside the treatment room and listen for interference when the monopole array is transmitting at full power.

The cross-sectional opening of the waveguide aperture is approximately 42 to 52 cm wide by 30 to 38 cm high to accommodate most patients. The monopole array waveguide applicator may be removable and may be fabricated using lightweight materials. For example, the applicators may be made with one or two different size apertures to accommodate most patient sizes. The waveguide aperture opening (along the axial or longitudinal direction of the patient) is approximately one-half of a wavelength. At 100 MHz, the wavelength in water is approximately 34 cm, thus one-half of a wavelength is about 17 cm. The E-field radiation is confined to be no larger than this 17-cm longitudinal region. The aperture opening can actually vary from about one-third of a wavelength to over one-half of a wavelength.

In the preferred embodiment, the power amplifiers in the deep thermotherapy system generate up to 400 to 600 Watts peak per channel in an eight channel system. Each of the power amplifiers in the deep thermotherapy system can be varied from zero watts to the maximum power level under computer control.

Monopole Phased Array Deep Heating System Design and Computer Simulation

Design of the radiating monopole elements for the deep thermotherapy array is as follows. The dielectric constant of deionized water at 100 MHz is approximately 78.0 and the electrical conductivity is approximately 0.0001 S/m. The wavelength is computed to be about 33.9 cm. Earlier, it was discussed that the spacing between the monopoles and the cavity backwall is about 8 cm, this corresponds to approximately 0.235 wavelengths. The theoretical length of each monopole radiating antenna element is typical one-quarter wavelength, or approximately 8.5 cm. In actually building the monopole array, one can use Type-N connectors and either solder a brass rod to the center pin of the connector, or actually replace the center pin of the connector with a brass rod to form the monopole radiator. The diameter of the brass rod antenna element can be 0.3175 cm, which is the same diameter as the center pin of a Type-N connector. A previous monopole array fabricated for 915 MHz operation used monopole elements having an electrical length of 0.34 wavelengths (Fenn et al, 1994 *International Symposium in Electromagnetic Compatibility, supra*). This 0.34 wavelength electrical length would be about 11.5 cm for 100 MHz operation, and this is the length chosen in the preferred embodiment. The desired frequency bandwidth determines the actual monopole length. The locations of the eight radiating monopole elements are tabulated in Table 1.

TABLE 1

Figure 15:
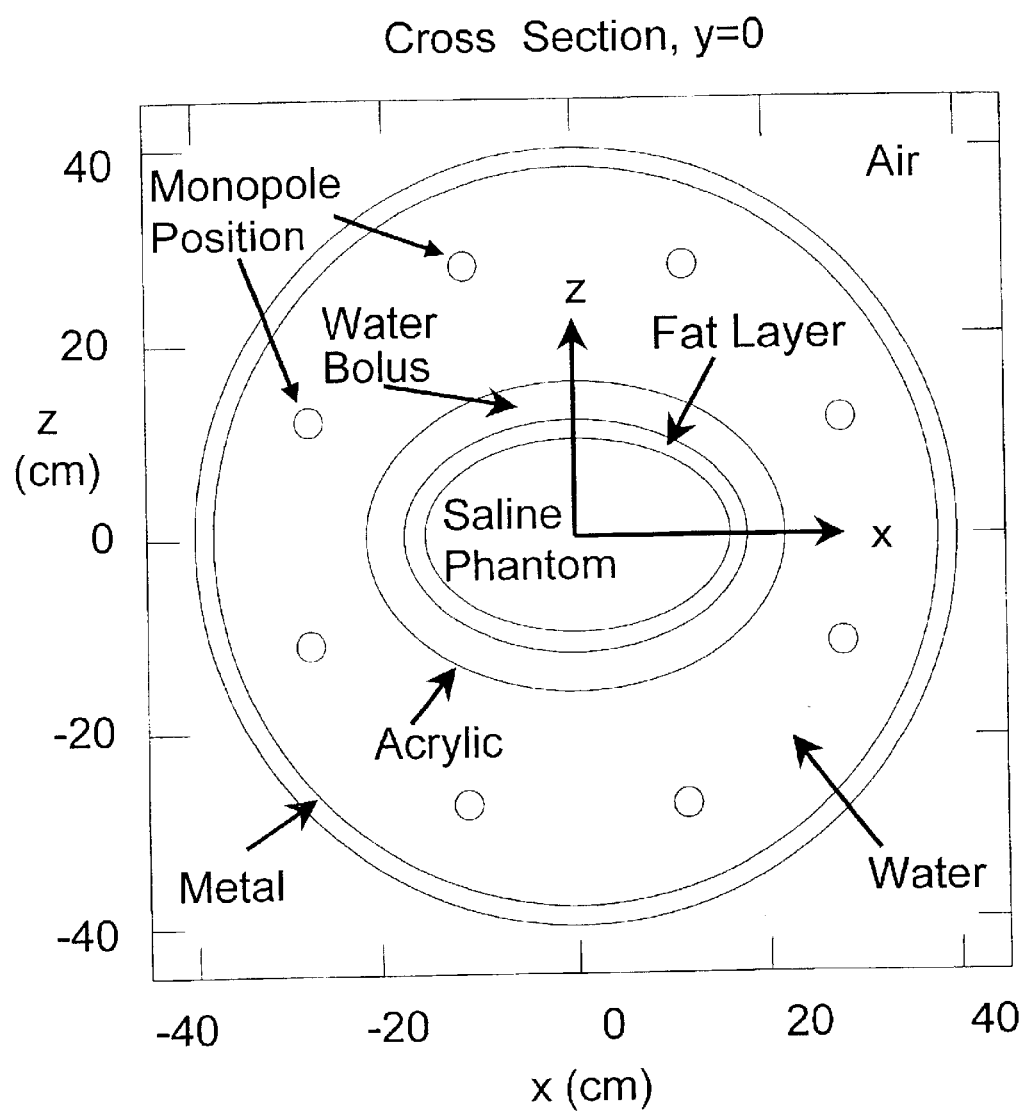
FIG. 15 schematically illustrates a monopole phased array applicator using saline as a homogeneous phantom muscle surrounded by a fat layer.

Element coordinates for monopole phased array for deep thermotherapy shown in FIG. 15.

| Element Number | x (cm) | z (cm) |
| --- | --- | --- |
| 1 | −11.5 | 27.7 |
| 2 | 11.5 | 27.7 |
| 3 | 27.7 | 11.5 |
| 4 | 27.7 | −11.5 |
| 5 | 11.5 | −27.7 |
| 6 | −11.5 | −27.7 |
| 7 | −27.7 | −11.5 |
| 8 | −27.7 | 11.5 |

To demonstrate the focused and confined radiation of the monopole array, the adaptive monopole phased array has been analyzed in detail using finite-difference time-domain (FDTD) code originally developed at Northwestern University. Several different monopole array applicators have been analyzed with a homogeneous muscle phantom (saline) surrounded by a fat layer (for example, as depicted in FIG. 15).

The monopole array theoretical heating performance is evaluated by calculating the specific absorption rate (SAR). Fundamentally, the SAR is expressed as $$SAR = c \, dT/dt \quad (2)$$

(where c is the specific heat of the tissue) and dT is the rise in the tissue temperature during the time interval dt. Equivalently, the SAR can be calculated as $$SAR = 0.5 \sigma |E|^2 / \rho \quad (3)$$

where $\sigma$ is the electrical conductivity of the tissue, $|E|$ is the electric field magnitude, and $\rho$ is the density of the tissue.

Figure 16:
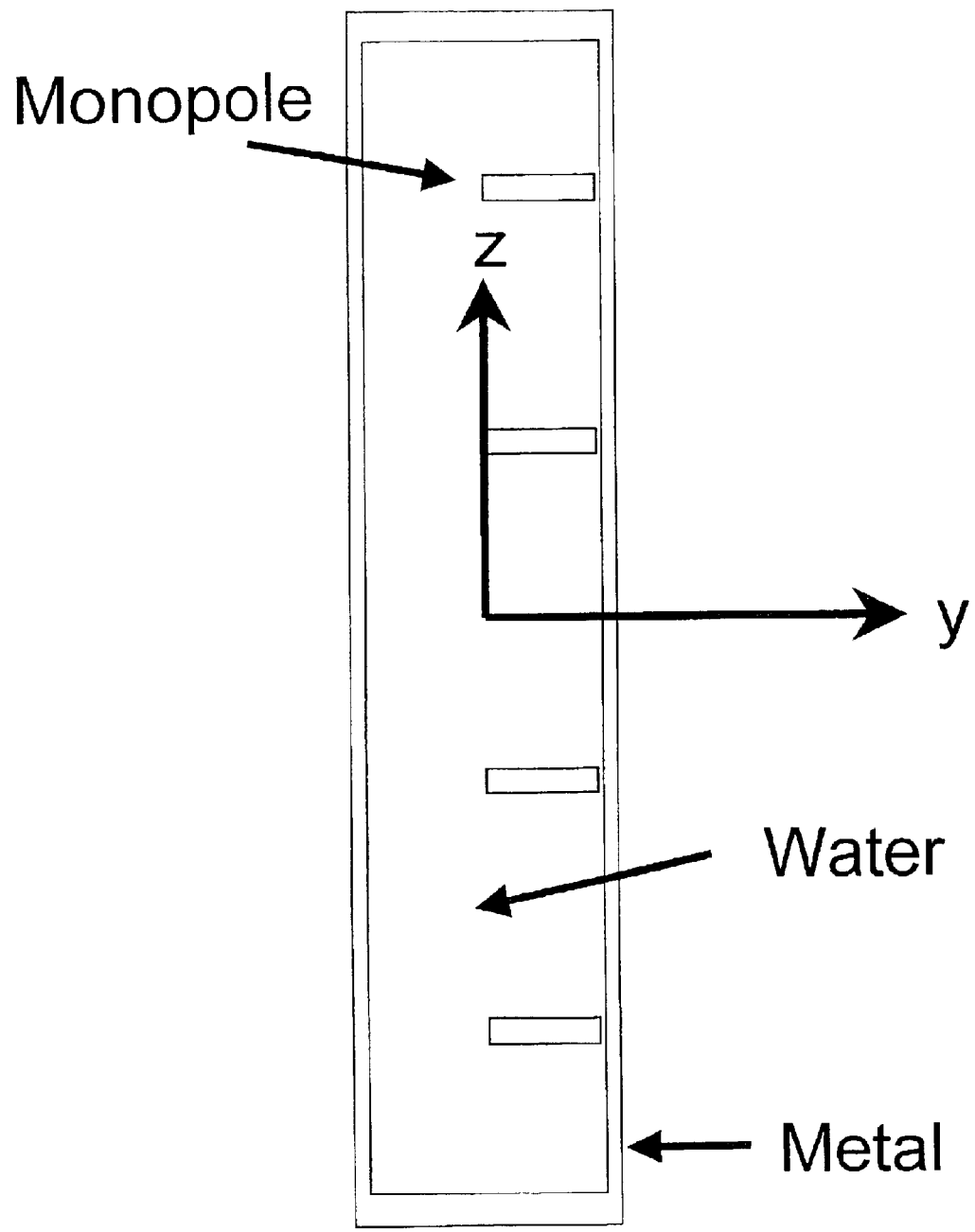
FIG. 16 is a side view of the monopole array according to FIG. 15.
Figure 17:
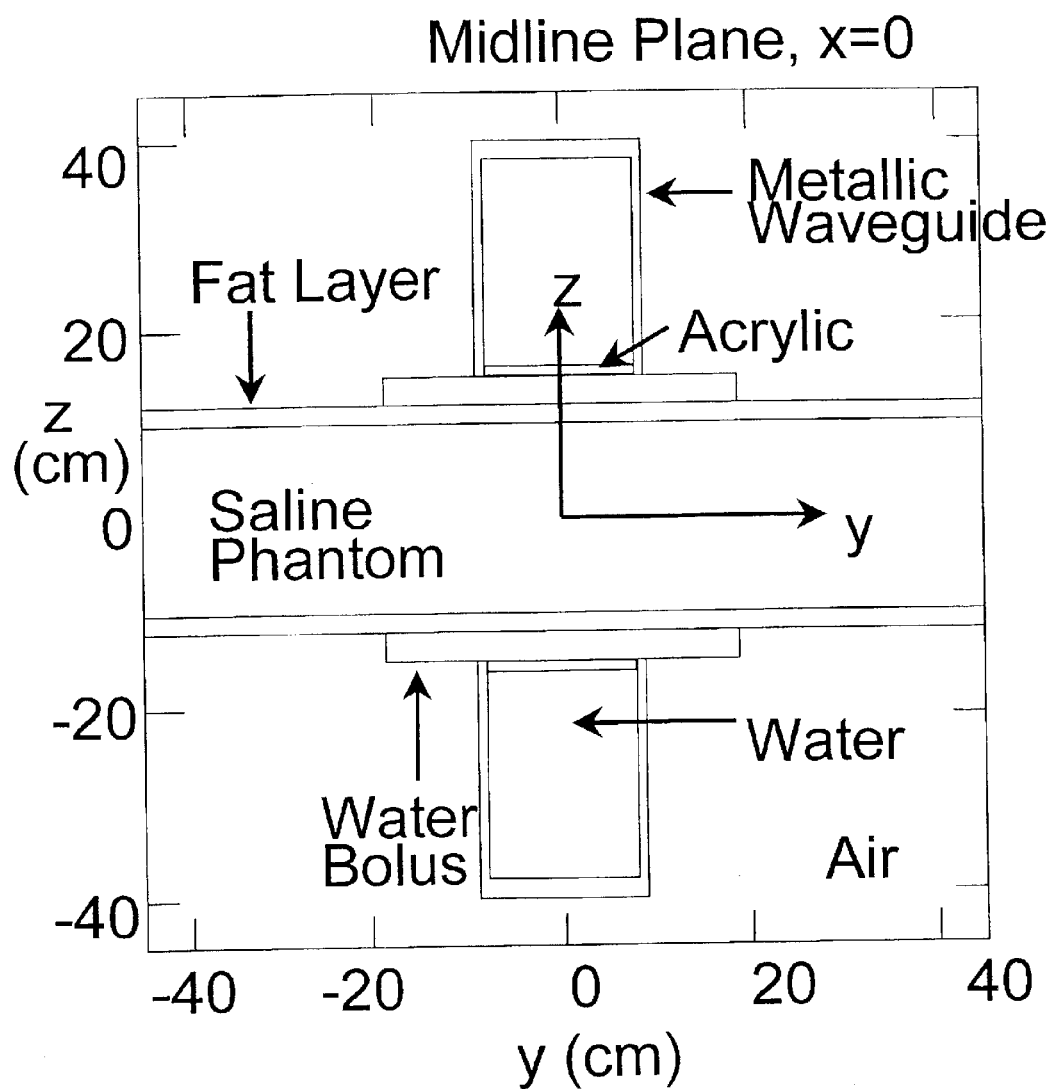
FIG. 17 is a side view of the thermotherapy applicator and saline phantom of FIG. 15.

The FDTD calculated results for one particular design for 100 MHz operation is now considered. In this example, the monopole elements are located in a ring 60 cm in diameter as shown in FIG. 15. The monopole array element coordinates are listed in Table 1. The monopole elements are surrounded by a circular-shaped water-filled metallic cavity having an inner diameter of 76 cm. Thus, the monopole elements are spaced 8 cm from the cavity backwall. The dielectric constant of water is 78.0 and the electrical conductivity is 0.0001 S/m at 100 MHz. The phantom muscle is modeled by saline (dielectric constant 77.0, conductivity 0.5 S/m), and the outer 2 cm of the phantom is modeled by a uniform layer of fat (dielectric constant 7.0, conductivity 0.07 S/m). The saline phantom muscle salinity s in parts per thousand (ppt) (grams salt per kg water) is s=9 g/kg or 9 ppt which is 0.9% NaCl in deionized water. The major axis of the elliptical phantom (including the fat layer) is 36 cm and the minor axis is 24 cm—this type of phantom has been used experimentally with an adaptive phased array applicator (Fenn et al., *The Journal of Oncology Management, supra*). The 3 cm space between the two ellipses encompassing the phantom is modeled by water (the water bolus). The outer ellipse may be modeled from an acrylic plastic material (dielectric constant 2.55, conductivity 0.0008 S/m), such as Rexolite® (lightweight, optically clear, cross-linked polystyrene, microwave plastic), which seals the aperture of the monopole array. The outer circle surrounding the monopole elements that radiate energy is modeled as a highly-conducting metal (dielectric constant 1.0, conductivity $3.72 \times 10^7$ S/m) such as aluminum. A side view of the monopole array is shown in FIG. 16—due to symmetry only four monopole elements are shown. A side view of the thermotherapy applicator and phantom in the midline plane (x=0) is shown in FIG. 17. The remaining medium surrounding the applicator and phantom is uniform air (dielectric constant 1.0, conductivity 0.0 S/m).

Figure 18:
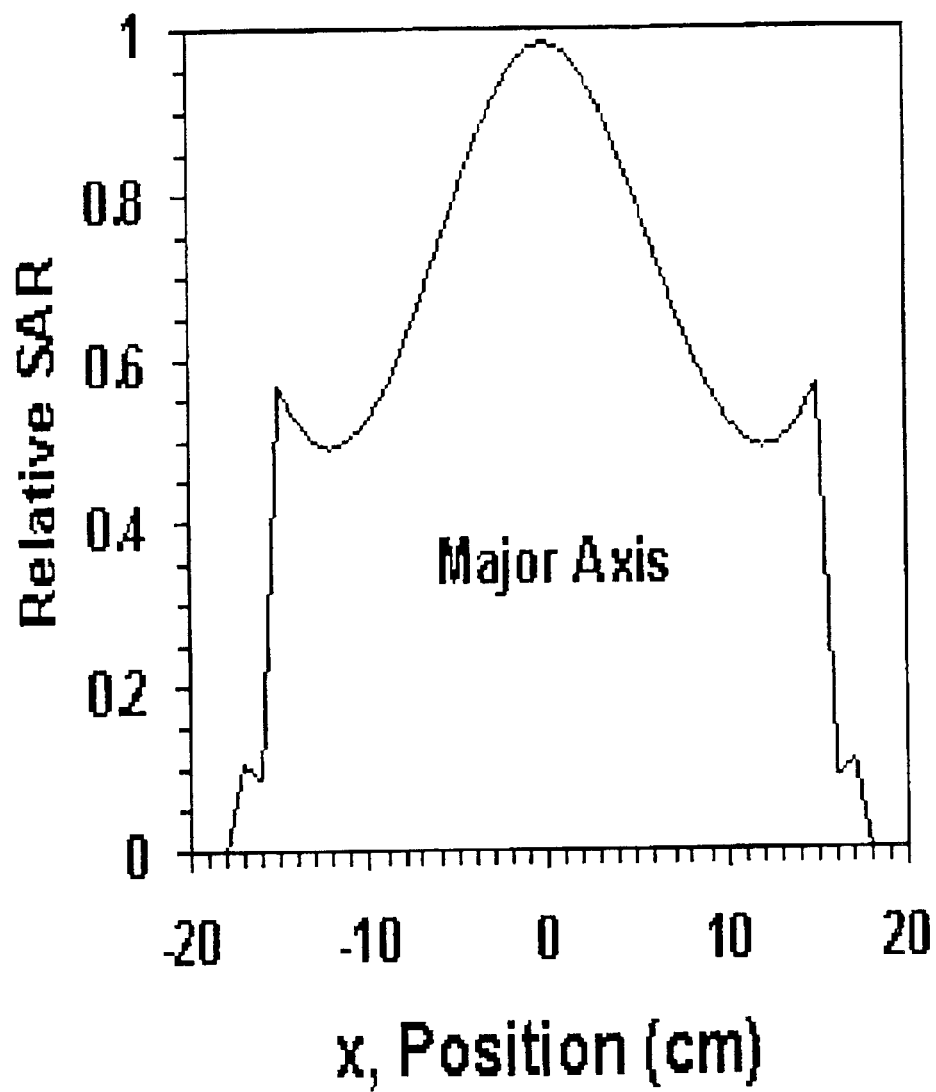
FIG. 18 is a graph showing the calculated SAR along the major axis of the elliptical phantom.
Figure 19:
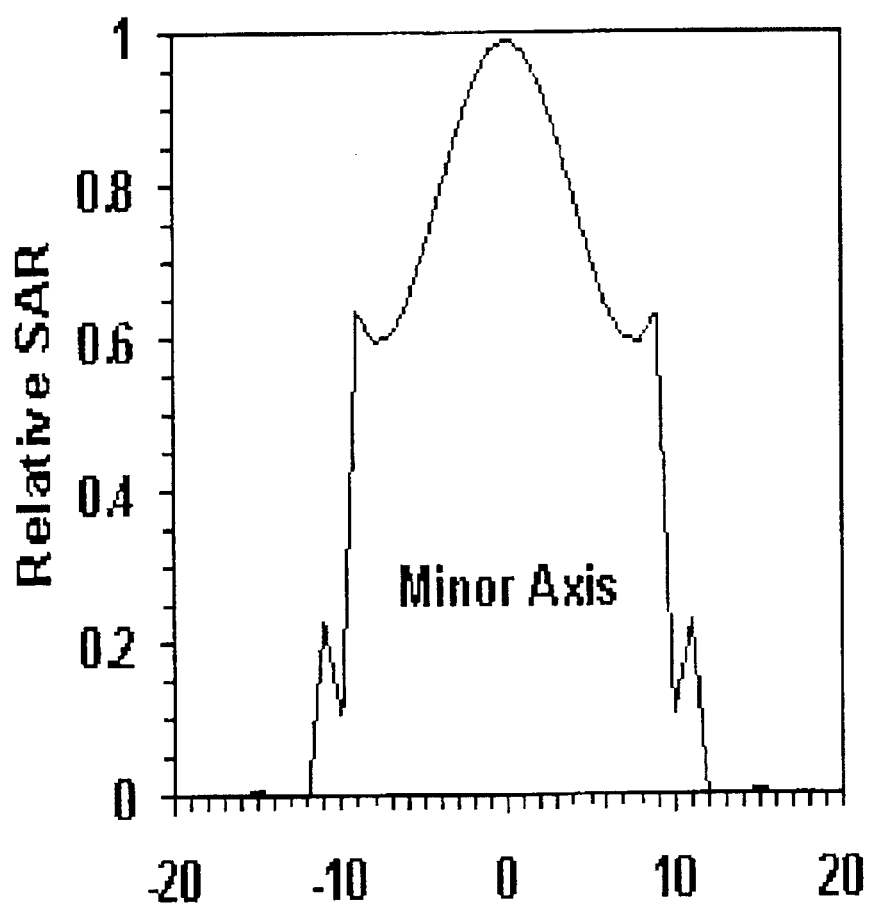
FIG. 19 is a graph showing the calculated SAR along the minor axis of the elliptical phantom.
Figure 20:
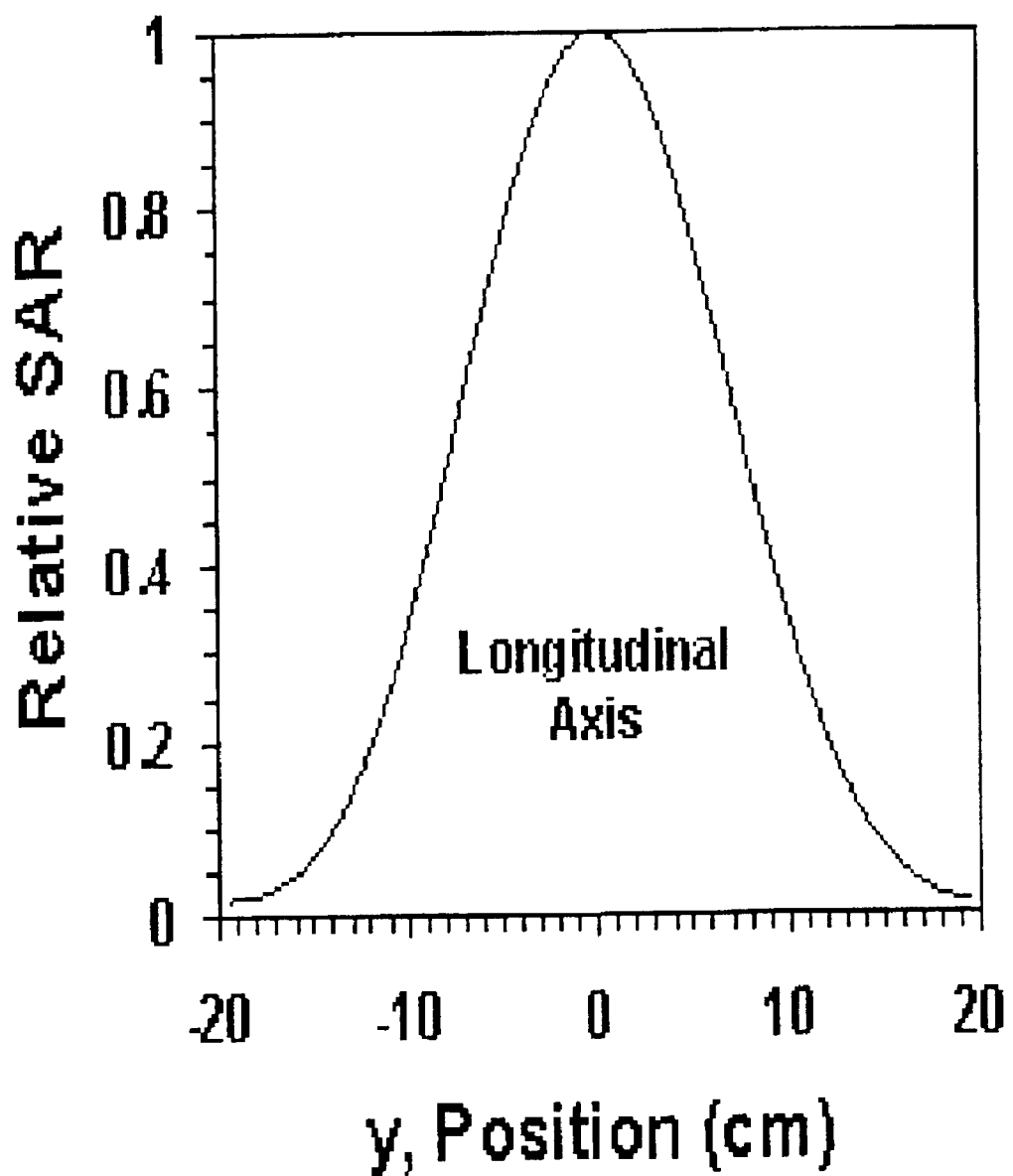
FIG. 20 is a graph showing the calculated SAR along the longitudinal axis of the elliptical phantom.
Figure 21:
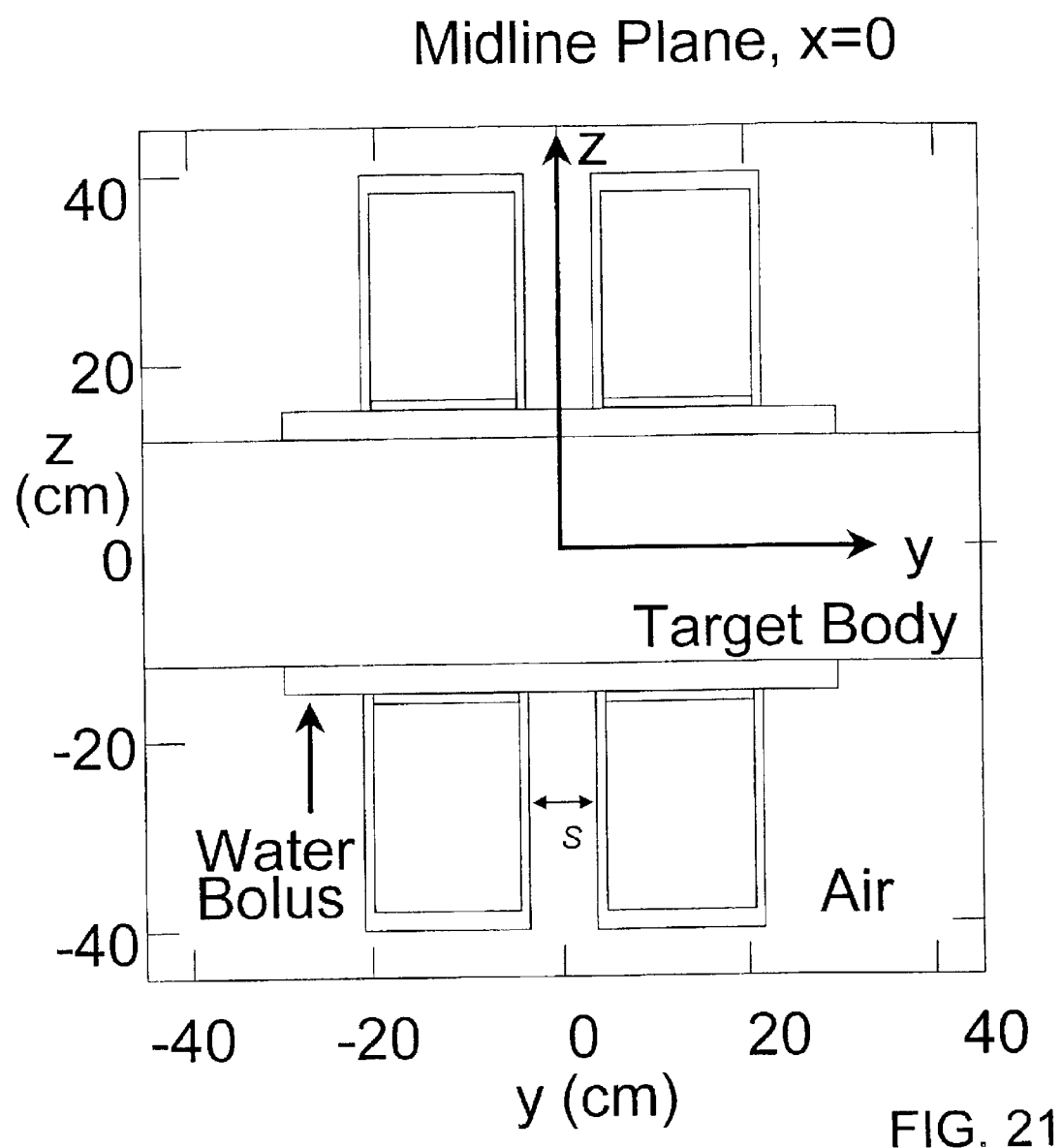
FIG. 21 is a side view showing another embodiment of the invention using two monopole array applicators separated by a distance.

For calculation purposes, the radiation frequency was selected as 100 MHz and the phase at each monopole was adjusted to focus the peak microwave signal at the midpoint of the phantom (0,0,0). FDTD software may be used to calculate the E-field amplitude and phase pattern for each monopole radiating one at a time, and then a second computer program may calculate (by superposition) the E-field radiation pattern and the specific absorption rate (SAR) pattern of the complete array. The graph shown in FIG. 18 plots the calculated SAR along the major axis of the elliptical phantom at y=0, z=0. The graph in FIG. 19 plots the calculated SAR along the minor axis of the elliptical phantom at x=0, y=0. FIG. 20 is a graph plotting the SAR values cut along the longitudinal axis of the phantom at x=0, z=0. The single peak along the major and minor axes indicates that the desired adaptively focused deep heating pattern is achieved. Further, the Gaussian (bell) shaped SAR pattern along the longitudinal axis indicates that 50% SAR is confined to about the width of the monopole array waveguide aperture (about 17 cm). A larger zone of heating in the longitudinal dimension is possible by providing two monopole array applicators separated by a distance s as depicted in FIG. 21. The two applicators can be fed coherently (with a common oscillator) or non-coherently (with separate oscillators).

Calculation of Equivalent Thermal Dose

A cumulative or equivalent thermal dose is often used to quantify the thermal dose given during thermotherapy treatments. The cumulative or total equivalent thermal dose relative to 43 degrees Celsius is calculated as a summation (Sapareto, S A and Dewey W C, Thermal Dose Determination in Cancer Therapy, *International Journal of Radiation Oncology Biology Physics*, Vol. 10, pp. 787–800, 1984):

$$t_{43°\ C.} \text{equivalent minutes} = \Delta t\ \Sigma R^{(43-T)}, \quad (4)$$

where $\Sigma$ is the summation over a series of temperature measurements during the treatment, T is the series of temperature measurements ($T_1, T_2, T_3, \ldots$), $\Delta t$ is the constant interval of time (units of seconds and converted to minutes) between measurements, R is equal to 0.5 if T>43° C. and R is equal to 0.25 if T<43° C. The equivalent thermal dose calculation is useful for assessing any possible heat damage to tissues including cancerous breast tissues, healthy skin, and other tissues. Equation 4 is a theoretical model developed by Sapareto and Dewey based on extensive in vitro and in vivo cell survival data, and the use of 43° C. for the reference temperature is a best estimate for when thermotherapy begins to cause a faster rate of cancer cell kill. Preferably, an equivalent thermal dose from approximately 30 to 120 minutes relative to 43 degrees Celsius may be delivered to the target tissue. As an example in the use of Equation 4, if the tissue temperature is maintained at 45° C. for 15 minutes, the equivalent thermal dose is calculated to be: $t_{43°\ C.} = 15 * 2^{(45-43)} = 15 * 4 = 60$ minutes. An equivalent thermal dose of 60 minutes relative to 43 degrees Celsius is often sufficient to achieve a therapeutic effect when used alone, or combined with thermosensitive liposome drug treatment, radiation therapy, chemotherapy, gene therapy, or drugs. In the preferred embodiment, the equivalent thermal dose is in the range of 30 to 120 minutes relative to 43 degrees Celsius.

Calculation of Radiofrequency Energy Dose

Electrical energy consumption is commonly expressed in units of kilowatt hours. Mathematically, the expression for the radiofrequency energy W delivered by an applicator is given by (Vitrogan, Elements of Electric and Magnetic Circuits, Rinehart Press, San Francisco, pp. 31–34, 1971):

$$W = \Delta t \Sigma P_i. \quad (1)$$

In the above equation, $\Delta t$ represents the constant intervals (in seconds) in which radiofrequency power is measured and the summation $\Sigma$ is over the complete treatment interval with the power (in Watts) in the ith interval denoted by $P_i$.

The radiofrequency energy W has units of watt-seconds, which is also designated as Joules. For example, in three consecutive 60-second intervals if the radiofrequency power is 500 watts, 400 watts, 600 watts, respectively, the total microwave energy delivered in 180 seconds is calculated as W=60 (500+400+600)=90,000 watt-seconds=90,000 Joules=90 kilojoules. A typical radiofrequency thermotherapy treatment with the monopole array applicator would use on the order of 1000 watts for a period of about 1800 seconds (30 minutes) which is equal to 1,800,000 Joules=1.8 megajoules. According to a preferred embodiment of the invention, a radiofrequency energy dose between 0.5 megajoules and 2.5 megajoules may be delivered to the monopole array applicator to therapeutically heat the target tissue.

Monopole Array Compatibility with Noninvasive Thermometry Techniques

Referring to FIG. 14, the sensor labeled 0 may include a combined E-field sensor to focus the RF field and a fiber-optic temperature sensor to measure the temperature in a single catheter. Temperature measurements at additional internal points would involve multiple invasive temperature sensors inserted into the tissue through catheters. To avoid the risk of tissue damage, infection, and pain that are associated with invasive thermometry methods, noninvasive techniques for measuring deep tissue temperatures during thermotherapy are very desirable. The monopole phased array 100 is compatible with most techniques developed in the literature for noninvasive thermometry of tissue including both RF and ultrasound passive radiometry, applied potential tomography, and active ultrasound imaging. A monopole array is compatible with magnetic resonance imaging techniques for non-invasive thermometry provided the monopole array waveguide cavity (bottom plate 125, top plate 130, and backwall 140) is made of a plastic material rather than metal. In a preferred embodiment, the radiofrequency monopole array can be used in a switched mode as a thermotherapy applicator and as a passive radiofrequency radiometer for noninvasive thermometry as described in U.S. Pat. No. 5,441,532 to Fenn. The monopole array applicator is compatible with applied potential tomography techniques (E. J. Gross and A. J. Fenn, "Applied Potential Tomography and Adaptive Control of Phased Microwave Systems," Proceedings of the 14th Annual Meeting of the North American Hyperthermia Society, Nashville, Tenn., Apr. 29, to May 4, 1994, p. 110).

Non-Coherent Mode of Operation

Figure 22:
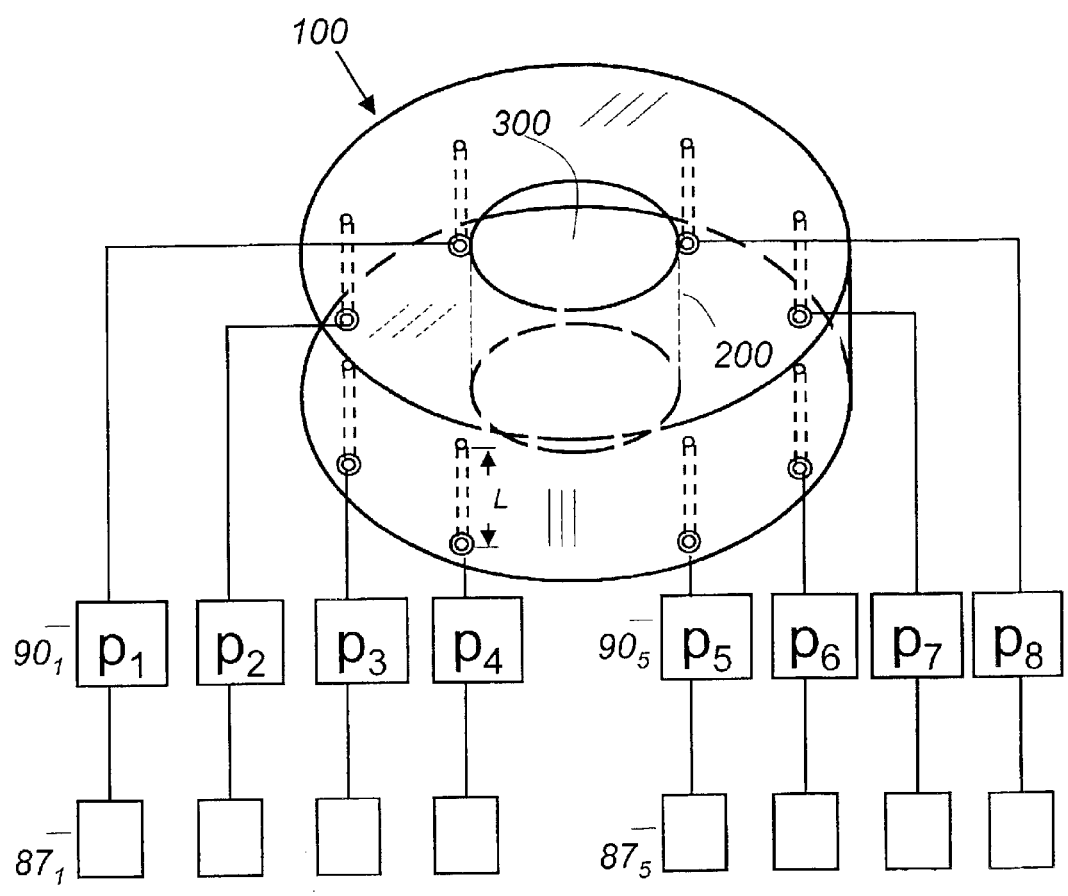
FIG. 22 schematically illustrates a monopole phased array applicator according to another embodiment of the invention.

In certain cases, particularly where uniform heating of tissue is desired, the monopole array 100 can be operated in non-coherent mode as depicted schematically in FIG. 22. In FIG. 22, independent waveform generators 87 such as CW oscillators drive each power amplifier 90 supplying RF power to the monopole array elements.

It is envisioned that certain applications may not require the full 360 degree monopole ring applicator. For treatment of some cancers, infectious diseases (e.g., AIDS), diabetes, psoriases, arthritis or other ailments that respond well to heat treatment, only a portion of the monopole ring may be activated or only half a ring, for example, may be fabricated. Depending on the area of the body to be heated, the selected monopole antenna elements may be activated and deactivated to heat the desired area. The ability to increase the number of monopole antenna elements in a single ring applicator or multiple ring applicators and to deactivate or activate certain monopole antenna elements theoretically should enable more accurate focusing or defocusing of an E-field to effectively heat the desired area of the body. Focussing or defocusing can be achieved by scanning the body (either by electronic phase shifter control or by mechanical scanning), and/or by deactivating or activating selected monopole antenna elements to achieve a temperature in the range of about 40 degrees to about 55 degrees in the targeted tissue of the body. It is envisioned that this monopole applicator may be used, as a heat alone treatment and/or to activate and release drugs and/or gene therapy. With such a monopole applicator, a prescribed area of the body may be treated with focused radiation and/or a larger regional area of the body may be heated.

The monopole antenna elements may be driven by RF phase shifter 80 and power amplifier 90 devices with RF signals that are pulsed in addition to having a constant power. It is believed that the pulsing of the RF signals will increase the intensity of heat delivered to the targeted tissue thereby activating or releasing drugs into the targeted tissue or enhancing gene therapy. The pulsing may also serve to open cell membranes, which may enhance drug delivery or gene therapy. Instead of an RF signal with constant power being delivered to the monopole elements, an RF signal with a varying frequency over the preferred range may be used to pulse the RF radiation delivered to the target body.

Equivalents

While the invention has been particularly shown and described with references to illustrated embodiments thereof, it will be understood by those skilled in the art that various changes in form and detail may be made therein without departing from the spirit and scope of the invention as defined by the appended claims.

What is claimed is:

1. A monopole phased array thermotherapy applicator radiating radiofrequency energy for inducing a temperature rise in a target within a body, comprising:
    a) a plurality of monopole elements each for transmitting electric-field radiation thereby radiating radiofrequency energy;
    b) a metallic waveguide with an RF reflecting ground plane surface with a plurality of circular holes for mounting the monopole elements, the metallic waveguide forming an aperture for receiving a body to be treated;
    c) a waveform generator providing a source of electric field coupled to each monopole radiating element through a respective phase and power weighting network;
    d) at least one electric field probe adapted to be positioned on a skin surface of the body for detecting electric field radiation from the plurality of monopole elements and transmitting feedback signals; and
    e) a controller circuit coupled to the electric field probe for receiving feedback signals to adjust the phase and power delivered to the plurality of monopole elements so that one or more adaptive nulls are to be formed on the surface of the body and a focus is formed at the target tissue to be treated with thermotherapy.

2. The apparatus of claim 1, wherein the radiofrequency energy is in the 80 to 150 MHz band.

3. The applicator of claim 1, wherein the monopole elements have a length between 7 cm and 12 cm.

4. The applicator of claim 1, wherein the monopole elements have a diameter approximately between 0.1 cm and 0.5 cm.

5. The applicator of claim 1, wherein the metallic waveguide structure encloses the plurality of monopole elements and forms an elliptical treatment aperture surrounding the body.

6. The applicator of claim 5, wherein a water bolus with cooled distilled or deionized water is used to couple the radiofrequency energy radiated by the monopole elements into the body.

7. The applicator of claim 5, wherein an air gap region surrounding skin not in contact with a water bolus is cooled by one of air-conditioned and room temperature air supplied by fans or tubes.

8. The applicator of claim 1, wherein the monopole elements are arranged in a ring with diameter approximately between 50 and 70 cm.

9. The applicator of claim 1, wherein the monopole elements are spaced between 6 and 10 cm from the reflecting ground plane surface, which is located circumferentially with respect to the plurality of monopole elements.

10. The applicator of claim 1, wherein the metallic waveguide, treatment aperture has a major axis of a length ranging from approximately 42 cm to 52 cm and a minor axis of a length approximately between 30 and 38 cm.

11. The applicator of claim 1, further comprising a flat non-conducting surface disposed within the treatment aperture of the monopole array applicator wherein a patient is supported on a flat non-conducting surface.

12. The applicator of claim 1, further comprising a Kevlar® or cloth surface supported by non-conducting cylindrical tubes within the treatment aperture of the monopole array applicator wherein a patient is supported on the Kevlar® or cloth surface supported by non-conducting cylindrical tubes within the treatment aperture of the monopole array applicator.

13. The applicator of claim 1, further comprising at least one temperature sensor positioned outside the body that senses the temperature of the body wherein feedback signals from the at least one electric field probe and the at least one temperature sensor outside the body are coupled to a computer controller circuit to control a phase shifter and power amplifier network to adjust the phase and power delivered to the monopole elements to form one or more nulls on the body's skin surface, while focusing radiofrequency energy at a deep tissue site within the body to heat the deep tissue site to the range from about 39 to about 46 degrees Celsius.

14. The applicator of claim 13, wherein a magnitude of the nulls formed on the body's skin surface and the focus in the tissue treatment region is controlled by an adaptive phased array fast acceleration gradient search computer algorithm that adjusts the phase and power delivered to the monopole elements.

15. The applicator of claim 14, wherein a radiofrequency energy dose between about 0.5 megajoules and about 2.5 megajoules is delivered to the monopole array applicator to therapeutically heat the target tissue.

16. The applicator of claim 14, wherein the internal tissue temperatures are monitored with an invasive temperature sensor placed in a catheter.

17. The applicator of claim 14, wherein the internal tissue temperatures are monitored noninvasively with one of passive radiofrequency radiometry, applied potential tomography, passive or active ultrasound radiometry or other noninvasive thermotherapy techniques.

18. The applicator of claim 14, wherein the applicator delivers an equivalent thermal dose of approximately 30 to 120 minutes relative to 43 degrees Celsius to the target tissue.

19. The applicator of claim 14, wherein the target tissue is one of precancerous, cancerous, benign, infected, arthritic, human immunodeficiency virus, and other diseased tissue.

20. The applicator of claim 13, wherein the focused radiofrequency energy heats tissue of the target to a temperature to release drug from thermosensitive liposomes circulating within the bloodstream in the vicinity of the target tissue.

21. The applicator of claim 20, wherein the target tissue is one of the liver, lung, breast, prostate, pancreas, stomach, rectum, colon, bladder, and other deep organs of the body.

22. The applicator of claim 13, wherein the focused radiofrequency energy heats the tissue of the target to a temperature to enhance the effectiveness of chemotherapy or drugs circulating within the bloodstream in the vicinity of the target tissue.

23. The applicator of claim 22, wherein the target tissue is one of the liver, lung, breast, prostate, pancreas, stomach, rectum, colon, bladder, and other deep organs of the body.

24. The applicator of claim 13, wherein the focused radiofrequency energy heats the tissue of the target to a temperature to enhance the effectiveness of radiation therapy delivered at the target tissue.

25. The applicator of claim 24, wherein the target tissue is one of the liver, lung, breast, prostate, pancreas, stomach, rectum, colon, bladder, and other deep organs of the body.

26. The applicator of claim 13, wherein the focused radiofrequency energy heats the tissue of the target to a temperature to enhance the effectiveness of gene therapy circulating within the bloodstream in the vicinity of the target tissue.

27. The applicator of claim 1, wherein each monopole element is driven non-coherently with separate oscillators.

28. The applicator of claim 1, further comprising a flat rigid support disposed within the aperture of the monopole array applicator wherein the body to be treated is supported within the aperture of the monopole array applicator by the flat rigid support.

29. The applicator of claim 1, further comprising a Kevlar® or cloth surface supported by non-conducting cylindrical tubes within the treatment aperture of the monopole array applicator wherein the body is supported within the aperture of the monopole array applicator by the Kevlar® or cloth material supported between two cylindrical rods.

30. The applicator of claim 1, further comprising a substantially rigid tube disposed within the matallic waveguide cavity wherein said substantially rigid tube is made of an acrylic plastic material so that an internal tissue temperature can be monitored noninvasively by one of magnetic resonance imaging, passive radiofrequency radiometry, applied potential tomography, passive or active ultrasound radiometry, and other noninvasive thermometry techniques.

31. A monopole phased array thermotherapy applicator according to claim 1, wherein a single applicator is used to induce the temperature rise in the target within the body.

32. A monopole phased array thermotherapy applicator according to claim 1, wherein two or more applicators are used to induce the temperature rise in the target within the body.

33. A monopole phased array thermotherapy applicator according to claim 1, further comprising an applicator support upon which the metallic waveguide rests or is suspended wherein the applicator support and metallic waveguide are moveable along at least one axis of the body.

34. A monopole phased array thermotherapy applicator according to claim 1, further comprising a non-conducting support for holding a body within the metallic waveguide aperture, the non-conducting support being moveably mounted within the metallic waveguide aperture.

35. A monopole phased array thermotherapy applicator according to claim 34, wherein the non-conducting support is mounted so that it is moveable along the x, y, and z axis of a target body.

36. A monopole phased array thermotherapy applicator according to claim 1, wherein the monopole elements are arranged in a ring with a diameter up to about 90 cm.

37. A monopole phased array thermotherapy applicator according to claim 1, wherein the metallic waveguide is made from one of aluminum and metallized fiberglass or plastic.

38. A monopole phased array thermotherapy applicator according to claim 37, wherein the metallized fiberglass or plastic is one of continuously metallized, and formed of conducting mesh or conducting wires.

39. A monopole phased array thermotherapy applicator according to claim 1, wherein the metallic waveguide forms a portion of a circle and the aperture for receiving the body is beneath an arc of the metallic waveguide.

40. A monopole phased array thermotherapy applicator according to claim 1, wherein the monopole elements form a ring about the body to be treated and the controller circuit activates and deactivates the monopole elements to focus the RF radiation at the target body.

41. A monopole phased array thermotherapy applicator radiating radiofrequency energy for inducing a temperature rise in a target within a body, comprising:
   a) a plurality of monopole elements each for transmitting electric-field radiation thereby radiating radiofrequency energy;
   b) a waveguide with an RF reflecting ground plane surface with a plurality of circular holes for mounting the monopole elements, the waveguide forming an aperture for receiving a body to be treated;
   c) a waveform generator providing a source of electric field coupled to each monopole radiating element through a respective phase and power weighting network;

d) at least one electric field probe adapted to be positioned on a skin surface of the body for detecting electric field radiation from the plurality of monopole elements; and e) a controller circuit coupled to the electric field probe for receiving feedback signals to adjust the phase and power delivered to the plurality of monopole elements so that one or more adaptive nulls are to be formed on the surface of the body and a focus is formed at the target tissue to be treated with thermotherapy, f) wherein the waveguide comprises a plastic material so that an internal tissue temperature can be monitored noninvasively by a technique selected from the group consisting of magnetic resonance imaging, passive radiofrequency radiometry, applied potential tomography, passive or active ultrasound radiometry, and other noninvasive thermometry techniques.

* * * * *